US011884765B2

(12) United States Patent
Hong et al.

(10) Patent No.: US 11,884,765 B2
(45) Date of Patent: Jan. 30, 2024

(54) BIODEGRADABLE ELASTIC HYDROGELS FOR BIOPRINTING

(71) Applicants: BOARD OF REGENTS, THE UNIVERSITY OF TEXAS SYSTEM, Austin, TX (US); NORTHEASTERN UNIVERSITY, Boston, MA (US)

(72) Inventors: Yi Hong, Irving, TX (US); Guohao Dai, Boston, MA (US); Cancan Xu, Arlington, TX (US); Wen-han Lee, Boston, MA (US)

(73) Assignees: BOARD OF REGENTS, THE UNIVERSITY OF TEXAS SYSTEM, Austin, TX (US); NORTHEASTERN UNIVERSITY, Boston, MA (US)

( * ) Notice: Subject to any disclaimer, the term of this patent is extended or adjusted under 35 U.S.C. 154(b) by 555 days.

(21) Appl. No.: 17/044,527

(22) PCT Filed: Apr. 2, 2019

(86) PCT No.: PCT/US2019/025344
§ 371 (c)(1),
(2) Date: Oct. 1, 2020

(87) PCT Pub. No.: WO2019/195256
PCT Pub. Date: Oct. 10, 2019

(65) Prior Publication Data
US 2021/0017319 A1 Jan. 21, 2021

Related U.S. Application Data

(60) Provisional application No. 62/652,726, filed on Apr. 4, 2018.

(51) Int. Cl.
*B33Y 10/00* (2015.01)
*B33Y 70/00* (2020.01)
(Continued)

(52) U.S. Cl.
CPC ........ *C08F 293/005* (2013.01); *B29C 64/118* (2017.08); *B33Y 10/00* (2014.12);
(Continued)

(58) Field of Classification Search
CPC . C08F 293/005; B29C 64/118; B29C 64/106; B33Y 10/00; B33Y 70/00;
(Continued)

(56) References Cited

U.S. PATENT DOCUMENTS

2004/0072799 A1* 4/2004 Li ........................... A61L 31/10
424/486
2008/0057128 A1* 3/2008 Li ........................ A61K 9/5153
514/6.9
(Continued)

FOREIGN PATENT DOCUMENTS

CN 1010837006 A 9/2010
EP 0863933 6/2001
(Continued)

OTHER PUBLICATIONS

Abdurrahmanoglu, Suzan, Volkan Can, and Oguz Okay. "Design of high-toughness polyacrylamide hydrogels by hydrophobic modification." Polymer 50.23 (2009): 5449-5455.
(Continued)

*Primary Examiner* — Nahida Sultana
(74) *Attorney, Agent, or Firm* — Meunier Carlin & Curfman LLC

(57) ABSTRACT

Disclosed herein are hydrogel compositions comprising a triblock copolymer having a formula A-B-A, wherein A is a polycaprolactone (PCL) block or a polyvalerolactone (PVL) block and B is a polyethylene glycol (PEG) block. Also disclosed are methods of making a hydrogel comprising providing a photoinitiator and a triblock copolymer having a formula A-B-A, wherein the triblock copolymer comprises
(Continued)

one or more ethylenically unsaturated moieties; and photocrosslinking the triblock copolymer, thereby forming a hydrogel. Also disclosed are methods of printing a three-dimensional (3D) article comprising extruding a printing composition from a deposition nozzle moving relative to a substrate, the printing composition comprising a photoinitiator and any herein disclosed triblock copolymer, wherein the triblock copolymer comprises one or more ethylenically unsaturated moieties; depositing one or more layers comprising the printing composition on the substrate; and photocrosslinking the triblock copolymer to form the printed 3D article.

11 Claims, 25 Drawing Sheets

(51) Int. Cl.
    *B29C 64/118*      (2017.01)
    *C08F 293/00*      (2006.01)
    *C12N 5/00*      (2006.01)
    *B29K 71/00*      (2006.01)
    *B29K 96/04*      (2006.01)
    *B29K 105/00*      (2006.01)

(52) U.S. Cl.
    CPC ............ *B33Y 70/00* (2014.12); *C12N 5/0012* (2013.01); *B29K 2071/02* (2013.01); *B29K 2096/04* (2013.01); *B29K 2105/0061* (2013.01); *B29K 2105/0085* (2013.01); *B29K 2995/006* (2013.01); *B29K 2995/0056* (2013.01); *C12N 2513/00* (2013.01); *C12N 2533/40* (2013.01)

(58) Field of Classification Search
    CPC .............. C12N 5/0012; C12N 2513/00; C12N 2533/40; B29K 2071/02; B29K 2096/04; B29K 2105/0061; B29K 2105/0085; B29K 2995/0056; B29K 2995/006
    See application file for complete search history.

(56) References Cited

U.S. PATENT DOCUMENTS

| 2013/0266508 | A1* | 10/2013 | Luo ....................... A61K 45/06 424/1.11 |
|---|---|---|---|
| 2016/0317621 | A1* | 11/2016 | Bright .................... A61B 90/30 |
| 2017/0136180 | A1 | 5/2017 | Zhao et al. |
| 2017/0217091 | A1 | 8/2017 | Hull et al. |
| 2018/0021140 | A1 | 1/2018 | Angelini et al. |

FOREIGN PATENT DOCUMENTS

| EP | 2231108 | 4/2015 |
|---|---|---|
| WO | 2003089506 | 10/2003 |

OTHER PUBLICATIONS

Almany, Liora, and Dror Seliktar. "Biosynthetic hydrogel scaffolds made from fibrinogen and polyethylene glycol for 3D cell cultures." Biomaterials 26.15 (2005): 2467-2477.
Arcaute, Karina, Brenda K. Mann, and Ryan B. Wicker. "Stereolithography of three-dimensional bioactive poly (ethylene glycol) constructs with encapsulated cells." Annals of biomedical engineering 34.9 (2006): 1429-1441.
Bakarich, Shannon E., et al. "Three-dimensional printing fiber reinforced hydrogel composites." ACS applied materials & interfaces 6.18 (2014): 15998-16006.
Bencherif, Sidi A., et al. "Influence of the degree of methacrylation on hyaluronic acid hydrogels properties." Biomaterials 29.12 (2008): 1739-1749.
Bertassoni, Luiz E., et al. "Direct-write bioprinting of cell-laden methacrylated gelatin hydrogels." Biofabrication 6.2 (2014): 024105.
Billiet, Thomas, et al. "The 3D printing of gelatin methacrylamide cell-laden tissue-engineered constructs with high cell viability." Biomaterials 35.1 (2014): 49-62.
Bukhari, Syed Majid Hanif, et al. "Synthesis and characterization of chemically cross-linked acrylic acid/gelatin hydrogels: effect of pH and composition on swelling and drug release." International Journal of Polymer Science 2015, 1-15.
Burdick, Jason A., et al. "Controlled degradation and mechanical behavior of photopolymerized hyaluronic acid networks." Biomacromolecules 6.1 (2005): 386-391.
Chuang, Tzu-Wen, and Kristyn S. Masters. "Regulation of polyurethane hemocompatibility and endothelialization by tethered hyaluronic acid oligosaccharides." Biomaterials 30.29 (2009): 5341-5351.
Cui, Xiaofeng, and Thomas Boland. "Human microvasculature fabrication using thermal inkjet printing technology." Biomaterials 30.31 (2009): 6221-6227.
Derakhshanfar, Soroosh, et al. "3D bioprinting for biomedical devices and tissue engineering: A review of recent trends and advances." Bioactive materials 3.2 (2018): 144-156.
Engler, Adam J., et al. "Matrix elasticity directs stem cell lineage specification." Cell 126.4 (2006): 677-689.
Fairbanks, Benjamin D., et al. "Photoinitiated polymerization of PEG-diacrylate with lithium phenyl-2,4,6-trimethylbenzoylphosphinate: polymerization rate and cytocompatibility." Biomaterials 30.35 (2009): 6702-6707.
Fedorovich, Natalja E., et al. "Three-dimensional fiber deposition of cell-laden, viable, patterned constructs for bone tissue printing." Tissue Engineering Part A 14.1 (2008): 127-133.
Gao, Guifang, et al. "Improved properties of bone and cartilage tissue from 3D inkjet-bioprinted human mesenchymal stem cells by simultaneous deposition and photocrosslinking in PEG-GelMA." Biotechnology letters 37.11 (2015): 2349-2355.
Gong, Chang Yang, et al. "Thermosensitive PEG-PCL-PEG hydrogel controlled drug delivery system: sol-gel-sol transition and in vitro drug release study." Journal of pharmaceutical sciences 98.10 (2009): 3707-3717.
Gong, Chang Yang, et al. "Synthesis and characterization of PEG-PCL-PEG thermosensitive hydrogel." International journal of pharmaceutics 365.1-2 (2009): 89-99.
Guilak, Farshid, et al. "Biomechanics and mechanobiology in functional tissue engineering." Journal of biomechanics 47.9 (2014): 1933-1940.
Hern, D. L.; Hubbell, J. A. Incorporation of Adhesion Peptides into Nonadhesive Hydrogels Useful for Tissue Resurfacing. J Biomed Mater Res. 1998, 39, 266-276.
Hoffman, Allan S. "Hydrogels for biomedical applications." Advanced drug delivery reviews 64 (2012): 18-23.
Hollister, Scott J. "Porous scaffold design for tissue engineering." Nature materials 4.7 (2005): 518-524.
Hölzl, Katja, et al. "Bioink properties before, during and after 3D bioprinting." Biofabrication 8.3 (2016): 032002.
Hong, Sungmin, et al. "3D printing of highly stretchable and tough hydrogels into complex, cellularized structures." Advanced materials 27.27 (2015): 4035-4040.
Hutmacher, Dietmar W. "Scaffolds in tissue engineering bone and cartilage." Biomaterials 21.24 (2000): 2529-2543.
Inzana, Jason A., et al. "3D printing of composite calcium phosphate and collagen scaffolds for bone regeneration." Biomaterials 35.13 (2014): 4026-4034.
Knowlton, Stephanie, et al. "3D-printed microfluidic chips with patterned, cell-laden hydrogel constructs." Biofabrication 8.2 (2016): 025019.
Kutty, Jaishankar K., et al. "The effect of hyaluronic acid incorporation on fibroblast spreading and proliferation within PEG-diacrylate based semi-interpenetrating networks." Biomaterials 28.33 (2007): 4928-4938.

(56) References Cited

OTHER PUBLICATIONS

Lee, Kuen Yong, and David J. Mooney. "Alginate: properties and biomedical applications." Progress in polymer science 37.1 (2012): 106-126.

Lee, Sang Jin, et al. "Surface modification of 3D-printed porous scaffolds via mussel-inspired polydopamine and effective immobilization of rhBMP-2 to promote osteogenic differentiation for bone tissue engineering." Acta biomaterialia 40 (2016): 182-191.

Lee, Vivian, et al. "Design and fabrication of human skin by three-dimensional bioprinting." Tissue Engineering Part C: Methods 20.6 (2014): 473-484.

Li, Jun, Xiping Ni, and Kam W. Leong. "Injectable drug-delivery systems based on supramolecular hydrogels formed by poly (ethylene oxide) s and α-cyclodextrin." Journal of Biomedical Materials Research Part A: An Official Journal of The Society for Biomaterials, The Japanese Society for Biomaterials, and The Australian Society for Biomaterials and the Korean Society for Biomaterials 65.2 (2003): 196-202.

Lim, Khoon S., et al. "New visible-light photoinitiating system for improved print fidelity in gelatin-based bioinks." ACS biomaterials science & engineering 2.10 (2016): 1752-1762.

Lin, Kai-Feng, et al. "Low-temperature additive manufacturing of biomimic three-dimensional hydroxyapatite/collagen scaffolds for bone regeneration." ACS Applied Materials & Interfaces 8.11 (2016): 6905-6916.

Ma, Guilei, Bolong Miao, and Cunxian Song. "Thermosensitive PCL-PEG-PCL hydrogels: Synthesis, characterization, and delivery of proteins." Journal of applied polymer science 116.4 (2010): 1985-1993.

Majima, Tetsuro, Wolfram Schnabel, and Wilhelm Weber. "Phenyl-2, 4, 6- trimethylbenzoylphosphinates as water-soluble photoinitiators. Generation and reactivity of O□ Ṗ (C6H5)(O-) radical anions." Die Makromolekulare Chemie: Macromolecular Chemistry and Physics 192.10 (1991): 2307-2315.

Malda, Jos, et al. "25th anniversary article: engineering hydrogels for biofabrication." Advanced materials 25.36 (2013): 5011-5028.

Mariner, Peter D., et al. "Synthetic hydrogel scaffold is an effective vehicle for delivery of INFUSE (rhBMP2) to critical-sized calvaria bone defects in rats." Journal of Orthopaedic Research 31.3 (2013): 401-406.

Markstedt, Kajsa, et al. "3D bioprinting human chondrocytes with nanocellulose-alginate bioink for cartilage tissue engineering applications." Biomacromolecules 16.5 (2015): 1489-1496.

Murphy, Sean V., and Anthony Atala. "3D bioprinting of tissues and organs." Nature biotechnology 32.8 (2014): 773-785.

Nicodemus, Garret D., and Stephanie J. Bryant. "Cell encapsulation in biodegradable hydrogels for tissue engineering applications." Tissue Engineering Part B: Reviews 14.2 (2008): 149-165.

Park, Hansoo, et al. "Effect of swelling ratio of injectable hydrogel composites on chondrogenic differentiation of encapsulated rabbit marrow mesenchymal stem cells in vitro." Biomacromolecules 10.3 (2009): 541-546.

Schiraldi, Chiara, et al. "Development of hybrid materials based on hydroxyethylmethacrylate as supports for improving cell adhesion and proliferation." Biomaterials 25.17 (2004): 3645-3653.

Schuurman, Wouter, et al. "Gelatin-methacrylamide hydrogels as potential biomaterials for fabrication of tissue-engineered cartilage constructs." Macromolecular bioscience 13.5 (2013): 551-561.

Shi, Wentao, Ran He, and Yaling Liu. "3D printing scaffolds with hydrogel materials for biomedical applications." European Journal of BioMedical Research 1.3 (2015): 3-8.

Son, Kuk Hui, and Jin Woo Lee. "Synthesis and characterization of poly (ethylene glycol) based thermo-responsive hydrogels for cell sheet engineering." Materials 9.10 (2016): 854.

Suntornnond, Ratima, et al. "A highly printable and biocompatible hydrogel composite for direct printing of soft and perfusable vasculature-like structures." Scientific reports 7.1 (2017): 1-11, 16902.

Tibbitt, Mark W., and Kristi S. Anseth. "Hydrogels as extracellular matrix mimics for 3D cell culture." Biotechnology and bioengineering 103.4 (2009): 655-663.

Tuncaboylu, Deniz C., et al. "Tough and self-healing hydrogels formed via hydrophobic interactions." Macromolecules 44.12 (2011): 4997-5005.

Venugopal, Jayarama Reddy, et al. "Biomaterial strategies for alleviation of myocardial infarction." Journal of the Royal Society Interface 9.66 (2012): 1-19.

Wang, Xiaohong, et al. "Generation of three-dimensional hepatocyte/gelatin structures with rapid prototyping system." Tissue engineering 12.1 (2006): 83-90.

Wei, Junhua, et al. "3D printing of an extremely tough hydrogel." Rsc Advances 5.99 (2015): 81324-81329.

Wu, Jinglei, et al. "An injectable extracellular matrix derived hydrogel for meniscus repair and regeneration." Acta biomaterialia 16 (2015): 49-59.

Xu, Cancan, et al. "Development of dopant-free conductive bioelastomers." Scientific reports 6.1 (2016): 1-13, 34451.

Xu, Cancan, et al. "Highly elastic biodegradable single-network hydrogel for cell printing." ACS applied materials & interfaces 10.12 (2018): 9969-9979.

Xu, Cancan, et al. "Low-initial-modulus biodegradable polyurethane elastomers for soft tissue regeneration." ACS applied materials & interfaces 9.3 (2017): 2169-2180.

Xu, Cancan, et al. "Triggerable degradation of polyurethanes for tissue engineering applications." ACS applied materials & interfaces 7.36 (2015): 20377-20388.

Xu, Changxue, et al. "Scaffold-free inkjet printing of three-dimensional zigzag cellular tubes." Biotechnology and bioengineering 109.12 (2012): 3152-3160.

Xu, Tao, et al. "Hybrid printing of mechanically and biologically improved constructs for cartilage tissue engineering applications." Biofabrication 5.1 (2012): 015001.

Xu, Tao, et al. "Viability and electrophysiology of neural cell structures generated by the inkjet printing method." Biomaterials 27.19 (2006): 3580-3588.

Yang, Feichen, Vaibhav Tadepalli, and Benjamin J. Wiley. "3D printing of a double network hydrogel with a compression strength and elastic modulus greater than those of cartilage." ACS Biomaterials Science & Engineering 3.5 (2017): 863-869.

Yu, Yinxian, et al. "Fabrication and characterization of electrospinning/3D printing bone tissue engineering scaffold." RSC advances 6.112 (2016): 110557-110565.

Zhang, Chao, et al. "A novel single precursor-based biodegradable hydrogel with enhanced mechanical properties." Soft Matter 5.20 (2009): 3831-3834.

Zhang, Kaile, et al. "3D bioprinting of urethra with PCL/PLCL blend and dual autologous cells in fibrin hydrogel: An in vitro evaluation of biomimetic mechanical property and cell growth environment." Acta biomaterialia 50 (2017): 154-164.

International Search Report and Written Opinion issued in PCT/US2019/025344, dated Jul. 19, 2020, 10 pages.

Xu et al., "Highly Elastic Biodegradable Single-Network Hydrogel for Cell Printing", ACS Appl. Mater. Interfaces, 10, p. 9969-9979; Published: Feb. 16, 2018 (Feb. 16, 2018) (retrieved from Internet URL <https://pubs.acs.org/doi/pdf/10.1021/acsami.Bb01294>.

International Preliminary Report on Patentability issued in PCT/US2019/025344, dated Oct. 15, 2020, 8 pages.

\* cited by examiner

| Polymers | Compressive modulus (kPa) | Compressive stress at 80% strain (kPa) | Water absorption (%) |
|---|---|---|---|
| PEG-PCL(24K)-DA-10% | 8.5±2.7[a] | 85.3±6.4[a] | 1890±189[a] |
| PEG-PCL(24K)-DA-20% | 13.2±2.8[b] | 145.8±27.6[b] | 1090±96[b] |
| α-CD-4%/PEG-PCL(24K)-DA-10% | 13.0±4.9[b] | 167.4±31.5[b] | 2158±46[c] |
| α-CD-8%/PEG-PCL(24K)-DA-10% | 18.9±3.6[b,c] | 235.2±38.8[c] | 2859±162[d] |
| α-CD-4%/PEG-PCL(24K)-DA-20% | 20.2±3.6[c] | 275.4±24.3[c] | 1414±30[e] |
| α-CD-8%/PEG-PCL(24K)-DA-20% | 32.6±5.4[d] | 401.7±45.8[d] | 1749±202[a] |

*a, b, c, d and e represent significantly different groups for each characteristic.

| Polymers | Initial modulus (kPa) | Tensile strength (kPa) | Breaking strain (%) |
|---|---|---|---|
| PEG-PCL(24K)-DA-10% | 11.5±2.1[a] | 10.9±1.1[a] | 210±21[a] |
| PEG-PCL(24K)-DA-20% | 18.9±2.6[b] | 17.8±3.2[b] | 191±25[a] |
| α-CD-4%/PEG-PCL(24K)-DA-10% | 38.9±5.6[c] | 58.5±4.1[c] | 311±27[b] |
| α-CD-8%/PEG-PCL(24K)-DA-10% | 53.8±6.3[d] | 71.2±5.9[d] | 332±19[b] |
| α-CD-4%/PEG-PCL(24K)-DA-20% | 72.0±8.5[e] | 106.2±17.3[e] | 324±36[b] |
| α-CD-8%/PEG-PCL(24K)-DA-20% | 91.8±11.3[f] | 148.7±15.6[f] | 341±15[b] |

*a, b, c, d, e and f represent significantly different groups for each characteristic.

Molecular ratio of aCD to PEG

10% PEG-PCL-DA, 8% aCD = 19.51

10% PEG-PCL-DA, 4% aCD = 9.75

20% PEG-PCL-DA, 4% aCD = 4.88

BIODEGRADABLE ELASTIC HYDROGELS FOR BIOPRINTING

CROSS-REFERENCE TO RELATED APPLICATIONS

This is a national stage application filed under 35 U.S.C. § 371 of PCT International Application No. PCT/US2019/025344, filed on Apr. 2, 2019, entitled "Biodegradable Elastic Hydrogels for Bioprinting," which claims benefit of U.S. Provisional Application No. 62/652,726, filed Apr. 4, 2018, incorporated herein by reference in their entireties.

STATEMENT REGARDING FEDERALLY SPONSORED RESEARCH

This invention was made with government support under Grant No. 1554835 from the National Science Foundation, and Grant No. R21HD090680 from the National Institutes of Health. The Government has certain rights in the invention.

FIELD

The disclosure generally relates to polymeric hydrogels and their uses in 3D bioprinting and cell culture.

BACKGROUND

Bioprinting has gained a surge of interest in biomedical engineering field, since it combines biocompatible materials, cells and supportive components into printed constructs.[1] Today, non-biological printing is very successful to fabricate stiff biomaterial scaffold (without cells) such as osteo-inductive materials to match patients' anatomy for bone repair.[2-5] However, in soft tissue bioprinting which requires live cells inside the scaffolds, there are still significant challenges. Current cell printing of soft tissue uses biodegradable hydrogel materials which are either naturally-derived polymer, such as fibrin,[6] gelatin,[7] hyaluronic acid,[8,9] alginate,[10] agarose,[11] or synthetic polymers, such as poly (ethylene glycol) (PEG),[12,13] and methacrylated gelatin (GelMA),[14-16] or natural-synthetic composites.[17-19] However, these hydrogels are brittle and unstretchable due to lack of flexibility and elasticity, which cannot mimic the mechanical behavior of softness, stretchability and elasticity of human soft tissues such as skin, skeletal muscle, blood vessels and heart muscles. To make stretchable hydrogels, some groups have developed dual crosslinking-network hydrogel system to achieve high elasticity and mechanical strength,[20-22] but such dual network system using two crosslinking mechanisms significantly increase the difficulty and complexity in cell printing control and handling.

Other methods to form hydrogels having desirable properties for cell growth are quite complex and difficult to implement for cell printing. For example, a dual-network hydrogel consisting of PEG and sodium alginate was bioprinted into complex, cellularized structures with high stretchability and toughness.[20] However, the use of two crosslinking mechanisms for cell printing encounters challenges and limitations. Firstly, the preparation of two or more precursors before cell printing is tedious and time consuming. Secondly, in many cases, there is more than one external stimulus involved in the gelation process, such as temperature, light, ion concentration, and enzyme (thrombin), which increases the difficulty of cell printing. For example, to load cells into a polycaprolactone (PCL)/poly (lactide-co-caprolactone) (PLCL)/fibrin hydrogel during the cell printing process, a cooling system was required to maintain the bioprinter chamber at 18° C. to avoid the cells contacting the high temperature PCL and PLCL.[17] Hence, a single-component based hydrogel system which requires only one external stimulus for gelation and can be prepared and bioprinted in a simple manner would be highly desirable for cell printing applications. Additionally, biodegradable hydrogels with good mechanical strength and elasticity are desirable to mimic the resilient native soft tissues.[23]

The compositions and methods disclosed herein address these and other needs.

SUMMARY

The disclosed subject matter relates to polymeric hydrogels and their uses in 3D bioprinting and cell culture.

In some aspects, disclosed herein are hydrogel compositions comprising a triblock copolymer having a formula A-B-A, wherein A is a polycaprolactone (PCL) block or a polyvalerolactone (PVL) block and B is a polyethylene glycol (PEG) block. In some embodiments, the PEG block B has a molecular weight ranging from 2,000 Da to 100,000 Da. In some embodiments, A is a polycaprolactone (PCL) block. In some embodiments, the block A has a molecular weight ranging from 200 Da to 10,000 Da. In some embodiments, the PEG block B is a linear PEG polymer. In some embodiments, the triblock copolymer comprises one or more ethylenically unsaturated moieties (e.g., acrylate, methacrylate, crotonate, vinyl, or norbornene moieties). In some embodiments, the triblock copolymer is crosslinked by a free radical polymerization. In some embodiments, the hydrogel is a single-network matrix. In some embodiments, the composition is biodegradable and biocompatible. In some embodiments, the hydrogel further comprises one or more viable cells.

In some aspects, provided herein are methods of making a hydrogel comprising providing a photoinitiator and a triblock copolymer having a formula A-B-A, wherein A is a polycaprolactone (PCL) block or a polyvalerolactone (PVL) block, B is a polyethylene glycol (PEG) block, and wherein the triblock copolymer comprises one or more ethylenically unsaturated moieties (M); and photocrosslinking the triblock copolymer, thereby forming a hydrogel. In some embodiments, the triblock copolymer comprises one or more ethylenically unsaturated moieties (M) at each terminal end, thereby having the formula M-A-B-A-M. In some embodiments, the ethylenically unsaturated moiety can comprise an acrylate, methacrylate, crotonate, vinyl, or norbornene moiety. In some embodiments, the photoinitiator comprises lithium phenyl(2,4,6-trimethylbenzoyl) phosphinate (LAP). In some embodiments, the photocrosslinking occurs by exposure to a wavelength of light from about 380 nm to about 700 nm. In some embodiments, the photocrosslinking occurs by exposure to a wavelength of light from about 395 nm to about 405 nm. In some embodiments, the triblock copolymer is crosslinked by a free radical polymerization.

In some aspects, provided herein are methods of printing a three-dimensional (3D) article comprising extruding a printing composition from a deposition nozzle moving relative to a substrate, the printing composition comprising a photoinitiator and a triblock copolymer having a formula A-B-A, wherein A is a polycaprolactone (PCL) block or a polyvalerolactone (PVL) block, B is a polyethylene glycol (PEG) block, and wherein the triblock copolymer comprises one or more ethylenically unsaturated moieties (M); depositing one or more layers comprising the printing composition on the substrate; and photocrosslinking the triblock copolymer to form the printed 3D article. In some embodiments, the one or more layers are deposited in a predetermined pattern. In some embodiments, the printing composition further comprises one or more viable cells. In some embodiments, methods further comprise culturing the one or more viable cells after the photocrosslinking step. In some embodiments, the culturing step comprises applying a mechanical stressor to the hydrogel.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 4A shows compressive stress-strain curves of PEG-PCL-DA hydrogels. FIG. 4B shows tensile stress-strain curves of PEG-PCL-DA hydrogels. FIG. 4C shows cyclic stretching of PEG-PCL-DA hydrogels at 100% deformation for 10 cycles.

FIG. 5A shows fluorescence micrographs of live & dead stained 3T3 fibroblasts encapsulated in PEG-DA and PEG-PCL(24K)-DA hydrogels after 1 day and 3 days of culture. FIG. 5B is a graph showing cell viability calculated as percentage of live cells (green) from the live & dead staining images in FIG. 5A. FIG. 5C is a graph showing metabolic index of 3T3 fibroblasts encapsulated in PEG-DA and PEG-PCL(24K)-DA hydrogels.

FIG. 6A is a graph showing a viscosity curve of elastic PEG-PCL(24K)-DA precursor solution. FIG. 6B is a graph showing cell viability of different cell types in printed 10% elastic PEG-PCL(24K)-DA hydrogel. FIG. 6C is a set of fluorescence micrographs showing live/dead assay results performed after gel polymerization and after 7 days in culture (scale bars represent 500 μm). FIG. 6D is a graph showing effects of different needle sizes and precursor solution concentrations on viability of neonatal human lung fibroblasts. FIG. 6E is a graph showing effects of shear stress on cell viability evaluated immediately after printing. FIGS. 6F and 6G are images showing sample shapes printed using bioprinter using 21 gauge or 18 gauge needle sizes, in which the scale bars represent 2 mm (FIG. 6F) and 5 mm (FIG. 6G).

FIG. 7C is a schematic showing PEG-PCL-DA and PEG-DA hydrogel formation via visible-light initiated photopolymerization. TEA: triethylamine; RT: room temperature; LAP: photo-initiator lithium phenyl(2,4,6-trimethylbenzoyl) phosphinate.

FIG. 12A shows a table of compressive properties and water absorption. FIG. 12B shows a compressive Stress-strain curve. The initial moduli, compressive strengths at 80% strain and water absorption of α-CD/PEG-PCL-DA hydrogels increase with increasing α-CD concentration (from 0% to 8%) when the concentration of PEG-PCL(24K)-DA was fixed.

FIG. 13B shows tensile stress-strain curve. The initial moduli, tensile strengths and breaking strains of α-CD/PEG-PCL(24K)-DA hydrogels increased with increasing α-CD concentration (from 0% to 8%) when the concentration of PEG-PCL(24K)-DA was fixed.

FIG. 14A shows the dominant factor that determines viscosity of bioink is the ratio between PEG and α-CD. The lower the PEG/α-CD, the higher the viscosity. The concentration of PEG matters to a lesser degree. FIG. 14B shows strain sweep. There exists a crossover strain above which material behaves like a fluid. FIG. 14C shows rheological behavior during printing. FIGS. 14D-F shows various analyses of rheological properties.

FIG. 15A shows the ear shape. FIG. 15B shows stretching and releasing of the hydrogel.

DETAILED DESCRIPTION

Figure 1:
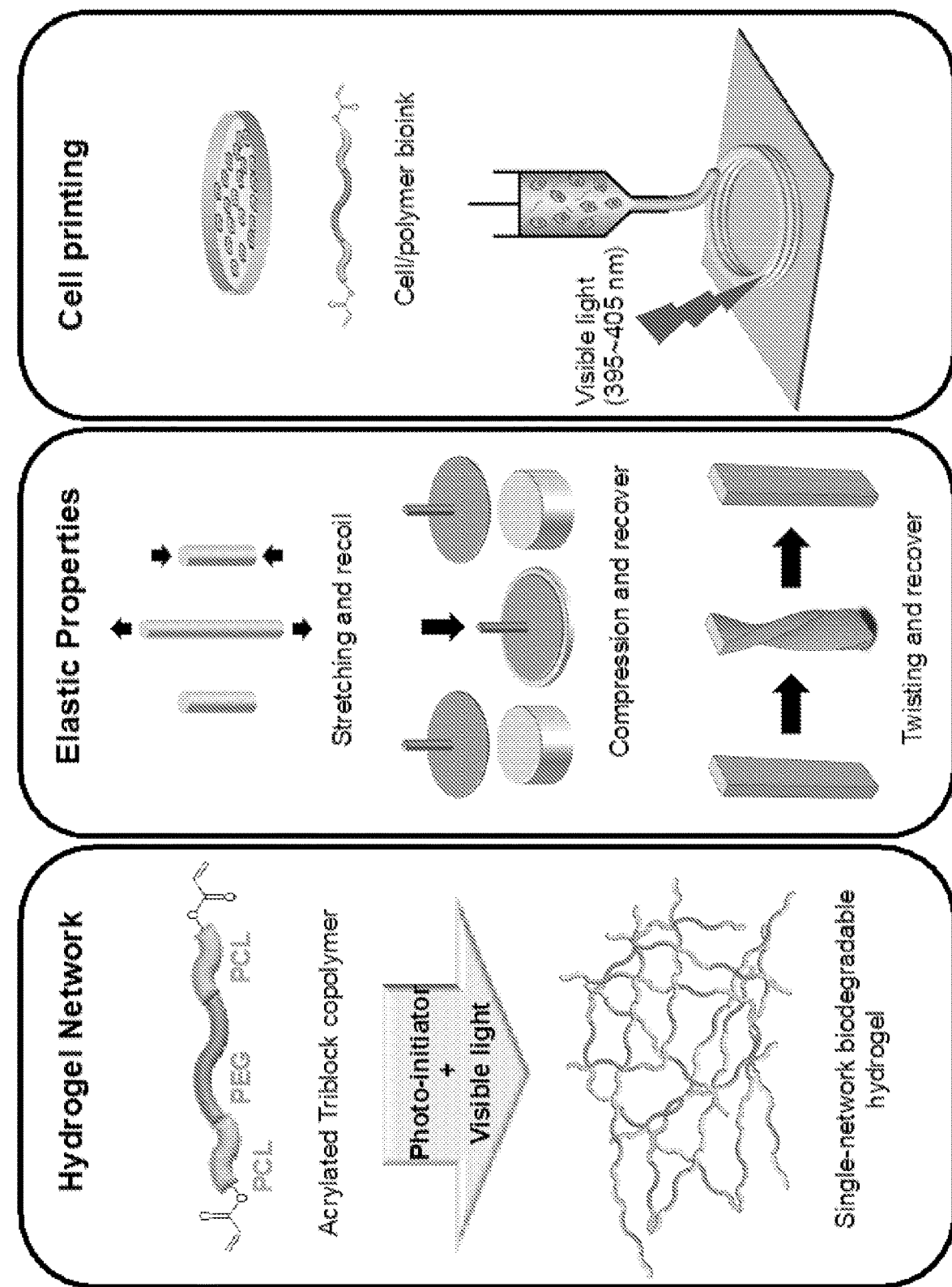
FIG. 1 is a schematic showing the preparation and characterization of highly elastic, visible-light crosslinked, single-network, biodegradable hydrogel for bioprinting. An acrylated PCL-PEG-PCL triblock polymer was synthesized, and then was crosslinked using visible light to form a highly elastic single network biodegradable hydrogel. The hydrogel has attractive mechanical properties, and it is stretchable, compressible and twistable. The hydrogel also can be bioprinted with various human cells, and form complex patterns upon visible-light exposure.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polymer is disclosed and discussed and a number of modifications that can be made to the polymer are discussed, specifically contemplated is each and every combination and permutation of the polymer and the modifications that are possible unless specifically indicated to the contrary. Thus, if a class of polymers A, B, and C are disclosed as well as a class of polymers D, E, and F and an example of a combination polymer, or, for example, a combination polymer comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a polymer "may include a moiety" is meant to include cases in which the polymer includes a moiety as well as cases in which the polymer does not include a moiety.

Ranges can be expressed herein as from "about" one particular value, and/or to "about" another particular value. When such a range is expressed, another embodiment includes from the one particular value and/or to the other particular value. As an example, a first range of from 1 to 10 and second range of from 3 to 7 also discloses at least a third range of from 1 to 7 and at least a fourth range of from 3 to 10. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, "molecular weight" refers to number-average molecular weight as measured by $^1$H NMR spectroscopy, unless clearly indicated otherwise.

Reference will now be made in detail to specific aspects of the disclosed materials, compounds, compositions, articles, and methods, examples of which are illustrated in the accompanying Examples.

Compositions

It is understood that the polymers and hydrogels of the present disclosure can be used in combination with the various compositions, methods, products, and applications disclosed herein.

Characteristics of ideal cell growth matrices include the ability to support cell growth while mimicking the in vivo growth environment the specific cell type typically encounters. In recent years, it has become apparent that in addition to environmental variables such as solute concentration, ionic strength, temperature, nutrient source type, proper culturing of many eukaryotic cell types also requires mimicking in vivo mechanical stressors. However, the prior art lacks methods to produce cell culture matrices such as hydrogels which support undamaged cell growth, are simple to perform, and can mimic an array of mechanical stressors.

The present disclosure provides advantages over the prior art by providing a simple system that closely mimics in vivo mechanical stressors and which avoids cell death or damage during the preparation process. The system employs a single crosslinking mechanism, thereby increasing control over and significantly simplifying the hydrogel preparation process. The crosslinking mechanism can use visible light, which avoids exposure of cells cultured in the hydrogel matrix to detrimental stimuli such as DNA-damaging ultraviolet light. Further, the entire growth-supporting hydrogel is comprised of biodegradable and biocompatible FDA-approved components, thereby facilitating use of cultured cells for subsequent in vivo applications (e.g., patient implantation). Additionally, the resultant hydrogel can be bioprinted and has high and tunable elasticity, flexibility, and strength and is therefore optimal for supporting growth of an array of cell types under changing mechanical conditions (e.g., soft tissue engineering). Further, the hydrogels are compatible with many other biomaterial approaches, such as incorporation of biomimetic peptides, proteins, growth factors or other bioactive molecules.

Disclosed herein are hydrogel compositions comprising a triblock copolymer having a formula A-B-A, wherein A is a polycaprolactone (PCL) block or a polyvalerolactone (PVL) block and B is a polyethylene glycol (PEG) block. The triblock copolymer is generally arranged by positioning a B block polymer as a middle block polymer in the formula A-B-A, and positioning an A block polymer on each side of the B block, thereby arriving at a linear triblock copolymer arrangement.

The triblock copolymer comprises at least three covalently bonded polymeric blocks identified in the formula A-B-A. Crosslinking the disclosed triblock copolymer can result in an elastic and flexible hydrogel. The triblock copolymer can comprise an array of polymeric materials within the spirit of the present disclosure. In some embodiments, one or more polymers in the triblock copolymer are biocompatible. A biocompatible polymer or other component is one which can be exposed to living cells or tissues without causing or otherwise resulting in substantive harm to the cells or tissues (e.g., being nontoxic or having negligible toxicity). In some embodiments, one or more polymers in the triblock copolymer are biodegradable. In some embodiments, one or more polymers in the triblock copolymer are Food and Drug Administration (FDA)-approved for human exposure or consumption, for example designated by the FDA as a Generally Recognized As Safe (GRAS) substance.

In some embodiments, the hydrogel is comprised of a plurality of triblock copolymer arranged in a repeating pattern, the repeating pattern being formed by a single photocrosslinking step which does not require additional crosslinking or chemical modification steps. Thus, in some embodiments, the hydrogel is a single-network matrix.

The triblock copolymer can be produced from a first block polymer (e.g., a PEG block), wherein the second block polymer is added as a polymeric block to the first block polymer. Alternatively, the second block polymer may be formed on the first block polymer (e.g., by polymerized addition of monomers of the second block polymer to the first block polymer). The third block polymer of the triblock copolymer can likewise be added as a polymeric block to another (e.g., a first or a second) block polymer or alternatively formed on another block polymer. The disclosure expressly contemplates the various combinations of providing and forming block polymers to arrive at a triblock copolymer, for example forming a first block polymer, then adding a second block polymer, then adding a third block polymer or, alternatively, joining a first, a second, and a third block polymer in a single reaction, or alternatively, joining a first and second block polymer and forming a third block polymer by polymerized monomeric addition, etc.

While the triblock copolymer comprises at least three polymeric blocks, and is hence referred to as a "triblock" copolymer. Typically, the polymeric blocks are covalently bonded to form the triblock copolymer. The triblock copolymer is amphiphilic and has a formula A-B-A, wherein A is generally more hydrophobic and less water soluble as compared to B. As such, B is generally more hydrophilic and more water soluble as compared to A. However, it is understood that the triblock copolymer can comprise additional polymeric blocks and/or additional non-polymeric components. In some embodiments, the triblock copolymer can comprise at least three, at least four, at least five, at least six, at least seven, at least eight, at least nine, or at least ten polymeric blocks.

For example, the triblock copolymer can comprise a set of one or more hydrophilic polymeric blocks flanked by one or more hydrophobic polymeric blocks at one terminus, and by one or more hydrophobic polymeric blocks at the other terminus. The three or more polymeric blocks are generally arranged according to the formula: one or more hydrophilic polymeric blocks-one or more hydrophobic polymeric blocks-one or more hydrophilic polymeric blocks. As non-limiting examples, the triblock copolymer can have a formula of A-HI-B-HI-A, HI-A-B-A-HI, A-HI-B-A-HI, A-HO-B-A, A-HO-B-HO-A, A-HI-HO-B-HO-HI-A, wherein HI and HO represent hydrophilic and hydrophobic polymeric blocks, respectively. It is expressly understood that a large number of combinations exist which permit the insertion of hydrophilic and/or hydrophobic polymeric blocks within the formula A-B-A, each of which are contemplated by the present disclosure. Inclusion of a hydrophilic block polymer flanked by hydrophobic block polymers can affect the balance between water absorption and desirable mechanical properties of the resultant hydrogel formed from the triblock copolymer. For example, inclusion of a hydrophilic polymer can increase water absorption to support cell growth, whereas inclusion of a hydrophobic polymer can enhance elasticity and flexibility to mimic in vivo mechanical stressors. In some embodiments, the overall triblock copolymer is water soluble.

The triblock copolymer has a formula A-B-A, wherein B is a polyethylene glycol (PEG) block. The PEG block B is at least slightly hydrophilic and water soluble. The PEG block B can be a linear PEG polymer or, alternatively, a branched PEG polymer. The PEG block B can range in size (molecular weight). In some embodiments, the PEG block B has a molecular weight ranging from about 2,000 Da to about 100,000 Da, or from about 2,000 Da to about 75,000 Da, or from about 2,000 Da to about 50,000 Da. In some embodiments, the PEG block B has a molecular weight ranging from about 5,000 Da to about 40,000 Da, from about 10,000 Da to about 30,000 Da, or from about 15,000 Da to about 25,000 Da. In some embodiments, the PEG block B has a molecular weight ranging from about 18,000 Da to about 22,000 Da, or a molecular weight of about 20,000 Da.

The PEG block B is not strictly limited to PEG alone and can comprise any one or more polymers which are at least slightly hydrophilic in addition to PEG. For example, other suitable hydrophilic polymeric blocks include poly(olefinic alcohol), poly(vinylpyrrolidone), poly(hydroxyalkylmethacrylamide), poly(hydroxyalkylmethacrylate), poly(saccharides), poly(a-hydroxy acid), poly(vinyl alcohol), polyphosphazene, polyoxazoline, poly(N-acryloylmorpholine), PEG derivates such as methoxypolyethylene glycol, copolymers thereof, among others. While the disclosed triblock copolymer comprises a PEG block B, it is expressly understood that the triblock copolymer can comprise any number of hydrophilic polymeric blocks which can substitute for PEG and which result in a hydrogel having desirable mechanical properties and capability for use in cell printing.

The triblock copolymer has a formula A-B-A, wherein A is a polycaprolactone (PCL) block or a polyvalerolactone (PVL) block. The A polymeric block can be a linear polymer or, alternatively, a branched polymer. The A polymeric block can range in size (molecular weight). In some embodiments, the A polymeric block has a molecular weight ranging from about 200 Da to about 10,000 Da, or from about 250 Da to about 7,500 Da, or from about 500 Da to about 5,000 Da. In some embodiments, the A polymeric block has a molecular weight ranging from about 750 Da to about 3,000 Da, from about 1,000 Da to about 2,500 Da, or from about 1,000 Da to about 2,000 Da. In some embodiments, the A polymeric block has a molecular weight ranging from about 1,000 Da to about 1,500 Da, or from about 1,500 Da to about 2,000 Da. In some embodiments, the A polymeric block has a molecular weight of about 1,100 Da or about 1,800 Da.

In some embodiments, the A polymeric block is a polycaprolactone (PCL) block. In some embodiments, the A polymeric block is a polyvalerolactone (PVL) block. In some embodiments, the A polymeric block is combination of a polycaprolactone (PCL) block and a polyvalerolactone (PVL) block. In some embodiments, the A polymeric block can comprise a copolymer. As a non-limiting example, the present disclosure includes examples of a triblock copolymer comprising PCL-PEG-PCL or PVL-PEG-PVL, but also examples a triblock copolymer comprising PVCL-PEG-PVCL, wherein PVCL refers to a copolymer of PVL and PCL.

Also disclosed herein is that the introduction of α-CD into the PEG-PCL-DA hydrogel network can greatly strengthen the mechanical properties of the PEG-PCL-DA hydrogel and improved good shear-thinning properties. This can be seen in FIGS. 10-15, which demonstrates the use of this elastic hydrogel for 3D bioprinting application.

The A polymeric block is not strictly limited to PCL or PVL alone and can comprise any one or more polymers which are at least slightly hydrophobic in addition to PCL or PVL. For example, other suitable hydrophobic polymeric blocks include polylactide (PLA), poly(lactic-co-glycolic acid) (PLGA), poly(L-lactide), poly(D,L-lactide), poly(D-lactide-co-glycolide), poly(L-lactide-co-glycolide), poly(D,L-lactide-co-glycolide), poly(lactide-co-caprolactone), polyhydroxybutyrate, polyhydroxyvalerate, poly(1,4-dioxan-2-one), poly-orthoester, biodegradable polyesters (e.g., polyglycolic acid (PGA), poly(ethylene succinate) (PESu), poly(propylene succinate) (PPSu), poly(butylene succinate) (PBSu), etc.), copolymers thereof, among others. While the disclosed triblock copolymer comprises an A polymeric block comprising polycaprolactone (PCL) or polyvalerolactone (PVL), it is expressly understood that the triblock copolymer can comprise any number of hydrophobic polymeric blocks which can substitute for PCL or PVL and which result in a hydrogel having desirable mechanical properties and capability for use in cell printing.

The triblock copolymer comprises at least two different polymers, according to the formula A-B-A. In some embodiments, the triblock copolymer comprises at least three, at least four, at least five, at least six, at least seven, at least eight, at least nine, or at least ten different polymers.

The triblock copolymer can comprise one or more ethylenically unsaturated moieties. Suitable ethylenically unsaturated moieties include acrylate, methacrylate, crotonate, vinyl, and norbornene moieties, among others. These moieties can be a pendant acrylate group attached to a side change of a monomer or it can be a terminal acrylate group attached to the ends of the polymer backbone. In some embodiments, the one or more ethylenically unsaturated moieties (e.g., acrylate, methacrylate, crotonate, vinyl, or norbornene moieties) are positioned on the A polymeric block. In some embodiments, the one or more ethylenically unsaturated moieties (M) are positioned at a terminal end of the A polymeric block, represented by the formula M-A-B-A-M, wherein M refers to an ethylenically unsaturated moiety (e.g., acrylate, methacrylate, crotonate, vinyl, or norbornene moiety).

The degree of substitution (DS) of the ethylenically unsaturated moiety (M), when a M moiety is present, can be from greater than zero % to 100%. In some embodiments, the DS of the M moiety can be from about 10% to about 90%, from about 20% to about 80%, from about 30% to about 70%, or from about 40% to about 60%. In some embodiments, the DS of the M moiety can be from about 50% to about 60%, from about 55% to about 60%.

In some embodiments, the triblock copolymer can be represented by the following formula 1:

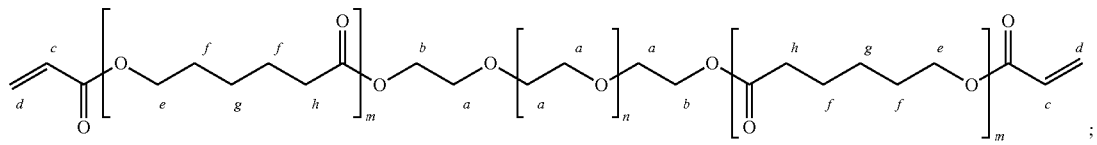

wherein m represents a number of units of the A polymeric block, and n represents a number of units of the B polymeric block. In some embodiments, m is an integer from 1 to 1,000, from 10 to 500, from 20 to 300, or from 25 to 100. In some embodiments, n is an integer from 1 to 10,000, from 50 to 5,000, from 100 to 1,000, or from 100 to 500. In some embodiments, the ratio of n:m is from about 1,000:1 to about 0.5:1, or from about 1,000:1 to about 5:1, or from about 1,000:1 to about 10:1, or from about 500:1 to about 10:1, or from about 500:1 to about 20:1, or from about 250:1 to about 50:1.

In some embodiments, the triblock copolymer is crosslinked by a free radical polymerization. For example, the triblock copolymer can be crosslinked by a photoinitiated reaction which crosslinks the ene groups of Acr moiety by a free radical polymerization.

Any one or more of the polymeric blocks of the triblock copolymer can contain from 0% to 100% pendancy. The term "pendancy" as used herein refers to the percentage of monomeric units in a polymer which contain a pendant group. Pendant groups are typically covalently attached either along the length of the PEG backbone, but can also be present at the terminus of a polymer chain. The pendant reactive groups can be attached to the PEG backbone directly or through a linking moiety, such as an alkylene group. In some embodiments, a polymeric block of the triblock copolymer comprises no pendant groups, or comprises from 1% to 100% pendancy, from 10% to 75% pendancy, or from 25 to 50% pendancy.

Without wishing to be bound by any one particular theory, the hydrogel is thought to be a matrix of relatively parallel triblock copolymers in which the termini of each individual triblock copolymer are covalently attached by a free radical polymerization to adjacent termini of an adjacent triblock copolymer. In some embodiments, in which the termini contain one or more acrylate, methacrylate, crotonate, vinyl, or norbornene moieties (M), it is thought that a covalent bond bridges adjacent M moieties on adjacent triblock copolymers.

The disclosed hydrogels are useful as scaffolds for cell or tissue growth. Thus, in some embodiments, the hydrogel further comprises one or more viable cells or tissues. In some embodiments, the one or more viable cells or tissues are cultured for use in patient transplants, transfusions, injections, or other medical procedures.

The disclosed hydrogels have excellent mechanical properties, including compression, water absorption, tensile strength, and other properties.

The hydrogel can have a maximum water absorption percentage of from about 1% to about 10,000%. In some embodiments, the hydrogel has a maximum water absorption percentage of from about 100% to about 7,500%, from about 250% to about 5,000%, from about 500% to about 4,000%, from about 750% to about 2,000%, or from about 900% to about 2,500%.

The hydrogel can have a compressive modulus of from about 1 kPa to about 200 kPa. In some embodiments, the hydrogel can have a compressive modulus of from about 2 kPa to about 100 kPa, from about 3 kPa to about 50 kPa, from about 4 kPa to about 40 kPa, or from about 5 kPa to about 25 kPa. In some embodiments, the hydrogel can have a compressive modulus of from about 5 kPa to about 20 kPa, or from about 10 kPa to about 25 kPa.

The hydrogel can have a compressive stress at 80% strain of from about 1 kPa to about 1,000 kPa. In some embodiments, the hydrogel can have a compressive stress at 80% strain of from about 10 kPa to about 800 kPa, about 25 kPa to about 600 kPa, about 40 kPa to about 400 kPa. In some embodiments, the hydrogel can have a compressive stress at 80% strain of from about 45 kPa to about 125 kPa, or about 75 kPa to about 350 kPa.

The hydrogel can have a tensile initial modulus of from about 0.1 kPa to about 100 kPa. In some embodiments, the hydrogel can have a tensile initial modulus of from about 0.5 kPa to about 75 kPa, from about 1 kPa to about 50 kPa, or from about 3 kPa to about 40 kPa. In some embodiments, the hydrogel can have a tensile initial modulus of from about 5 kPa to about 30 kPa, or from about 10 kPa to about 40 kPa.

The hydrogel can have a tensile strength of from about 0.1 kPa to about 100 kPa. In some embodiments, the hydrogel can have a tensile strength of from about 0.5 kPa to about 75 kPa, from about 1 kPa to about 50 kPa, or from about 5 kPa to about 40 kPa. In some embodiments, the hydrogel can have a tensile strength of from about 8 kPa to about 25 kPa, or from about 10 kPa to about 35 kPa.

The hydrogel can have a breaking strain percentage of from about 50% to about 500%. In some embodiments, the hydrogel has a breaking strain percentage of from about 75% to about 300%, from about 90% to about 250%, or from about 100% to about 200%. In some embodiments, the hydrogel has a breaking strain percentage of from about 145% to about 175%, or from about 150% to about 200%.

The hydrogel can have a suture retention of from about 0.05 N/mm$^2$ to about 1 N/mm$^2$. In some embodiments, the hydrogel can have a tensile strength of from about 0.08 N/mm$^2$ to about 0.8 N/mm$^2$, from about 0.1 N/mm$^2$ to about 0.6 N/mm$^2$, or from about 0.15 N/mm$^2$ to about 0.5 N/mm$^2$. In some embodiments, the hydrogel can have a tensile strength of from about 0.18 N/mm$^2$ to about 0.22 N/mm$^2$, or from about 0.26 N/mm$^2$ to about 0.38 N/mm$^2$.

The hydrogel can have an instant recovery percentage of from about 10% to about 200%. In some embodiments, the hydrogel has an instant recovery percentage of from about 50% to about 150%, from about 90% to about 110%, or from about 95% to about 105%. In some embodiments, the hydrogel has an instant recovery percentage of from about 98% to about 100%, or from about 99% to about 101%.

Methods for Making Hydrogels

Also disclosed herein are methods of making a hydrogel comprising: a) providing a composition comprising a photoinitiator and a triblock copolymer having a formula A-B-A, wherein A is a polycaprolactone (PCL) block or a polyvalerolactone (PVL) block, B is a polyethylene glycol (PEG) block, and wherein the triblock copolymer comprises one or more ethylenically unsaturated moieties; and b) photocrosslinking the triblock copolymer, thereby forming a hydrogel.

One or more monomers of a polymer in the triblock copolymer can comprise a moiety (M) that is an ethylenically unsaturated moiety. In some embodiments, the ethylenically unsaturated moiety is crosslinkable, for example by photocrosslinking (e.g., visible light, ultraviolet-light), redox chemistries (e.g., TEMED/APS), sulfhydryl-reactive chemistries (e.g., thiol-maleamide, thiol-norbornene), click chemistries, or other crosslinking methodologies. In some embodiments, one or more monomers of a polymer in the triblock copolymer can comprise one or more acrylate, methacrylate, crotonate, vinyl, or norbornene moieties (M). In some embodiments, one or more monomers of a polymer in the triblock copolymer can comprise one or more acrylate, methacrylate, or crotonate moieties (M). In some embodiments, acrylate is selected. In some embodiments, the ethylenically unsaturated moiety is positioned on the A polymeric block. In some embodiments, the ethylenically unsaturated moiety is positioned at a terminal end of the A polymeric block (i.e., a terminal moiety), represented by the formula M-A-B-A-M, wherein M refers to an ethylenically unsaturated moiety (e.g., an acrylate, methacrylate, crotonate, vinyl, or norbornene moiety).

In some embodiments, the M moiety is an acrylate. The acrylate donor used to form an acrylated triblock copolymer is not particularly limited and can include donors of monoacrylates, oligoacrylates, or polyacrylates. In some embodiments, the acrylate donor comprises acryloyl chloride.

The composition comprising the photoinitiator and the triblock copolymer can comprise the triblock copolymer in an amount ranging from about 1 weight percent (wt %) to about 99 wt %. In some embodiments, the composition comprises the triblock copolymer in an amount ranging from about 5 wt % to about 80 wt %, from about 10 wt % to about 70 wt %, from about 10 wt % to about 60 wt %, from about 10 wt % to about 50 wt %, or from about 10 wt % to about 40 wt %. In some embodiments, the composition comprises the triblock copolymer in an amount of about 10 wt %, about 20 wt %, or about 40 wt %.

The photoinitiator can be any photoinitiator capable of catalyzing a reaction which polymerizes the triblock copolymer. In some embodiments, the photoinitiator is a visible light-activated photoinitiator. In some embodiments, the photoinitiator is activated by a wavelength of light from about 380 nm to about 700 nm. In some embodiments, the photoinitiator is activated by a wavelength of light from about 380 nm to about 600 nm, from about 380 nm to about 500 nm, from about 380 nm to about 450 nm, from about 395 nm to about 450 nm, or from about 395 nm to about 405 nm. As such, the photocrosslinking step can occur by exposure to a wavelength of light from about 380 nm to about 600 nm, from about 380 nm to about 500 nm, from about 380 nm to about 450 nm, from about 395 nm to about 450 nm, or from about 395 nm to about 405 nm. In some embodiments, the triblock copolymer is crosslinked by a free radical polymerization.

In some embodiments, the photoinitiator is a visible light-activated photoinitiator capable of photoinitiating a crosslinking reaction between two or more ethylenically unsaturated moieties (e.g., acrylate, methacrylate, crotonoate, vinyl, and/or norbornene groups). In some embodiments, the photoinitiator comprises lithium phenyl(2,4,6-trimethylbenzoyl) phosphinate (LAP), Eosin Y (EY, photosensitizer), triethanolamine (TEOA, initiator), 1-vinyl-2-pyrrolidinone (VP, catalyst), or a green light initiator at 530 nm. Inclusion of a visible light-activated photoinitiator facilitates single-step 3D printing of a hydrogel comprising cells or tissues because wavelengths of visible light do not damage cells and tissues in the manner that other wavelengths of light can. Thus, inclusion of a visible light-activated photoinitiator facilitates combining cells/tissues with the triblock copolymer prior to photocrosslinking. Therefore, a first step of crosslinking followed by a second step of adding cells or tissues is not required.

The photoinitiator, however, is not limited to visible light-activated photoinitiators and can alternatively comprise photoinitiators activated by non-visible light wavelengths (e.g., ultraviolet light). Additional non-limiting photoinitiators include benzophenones, acetophenone derivatives, such as alpha-hydroxyalkylphenylketones, benzoin alkyl ethers, benzil ketals, monoacylphosphine oxides, and bis-acylphosphine oxides, mercaptobenzothiazoles, mercaptobenzooxazoles and hexaryl bisimidazole. More specific photoinitiators include ethyl 2,4,6-trimethylbenzoylphenyl phosphinate (Lucirin TPO-L), benzophenone (IRGACURE 500), 1-hydroxy-cyclohexyl-phenyl-ketone (IRGACURE 184), 2-hydroxy-2-methyl-1-phenyl-1-propanone (DAROCUR 1173), 2,2-dimethoxy-2-phenyl acetophenone (IRGACURE 651), 2-Hydroxy-1-[4-(2-hydroxyethoxy)phenyl]-2-methyl-1-propanone (IRGACURE 2959), Methyl benzoylformate (DAROCUR MBF), oxy-phenyl-acetic acid 2-[2-oxo-2-phenyl-acetoxy-ethoxy]-ethyl ester and oxy-phenyl-acetic 2-[2-hydroxy-ethoxy]-ethyl ester (IRGACURE 754), alpha, alpha-dimethoxy-alpha-phenylacetophenone (IRGACURE 651), 2-benzyl-2-(dimethyl-amino)-1-[4-(4-morpholinyl) phenyl]-1-butanone (IRGACURE 369), 2-methyl-1-[4-(methylthio)phenyl]-2-(4-morpholinyl)-1-propanone (IRGACURE 907), and diphenyl (2,4,6-trimethylbenzoyl)-phosphine oxide (DAROCUR TPO).

The composition can comprise the photoinitiator in an amount from about 0.01 weight percent (wt %) to about 10 wt %. In some embodiments, the composition can comprise the photoinitiator in an amount from about 0.1 wt % to about 8 wt %, or from about 0.1 wt % to about 6 wt %, or from about 0.5 wt % to about 5 wt %.

The compositions can further comprise additives, particularly additives useful for 3D printing. Non-limiting examples of additives include diluent synthetic polymers (e.g., PEG, polypropylene glycol, poly(vinyl alcohol), poly (methacrylic acid)), therapeutics (e.g., antibiotics such as penicillin and streptomycin), cell nutrients (e.g., proteins, peptides, amino acids, vitamins, carbohydrates (e.g., starches, celluloses, glycogen), and minerals (e.g., calcium, magnesium, iron), synthetic or naturally occurring peptides, nucleic acids, surfactants, plasticizers, salts (e.g., sodium chloride, potassium chloride, phosphate salts, acetate salts), viable/living cells, and cell components (e.g., elastin, fibrin, proteoglycans). The compositions can comprise one or more additives in an amount of 0 wt % to about 95 wt % of the composition, based on total weight of the composition. In some embodiments, the compositions comprise one or more additives in an amount up to about 75 wt %, up to about 50 wt %, up to about 40 wt %, or up to about 25 wt %.

The photocrosslinking reaction should occur for a sufficient period of time to photocrosslink the triblock copolymer. A portion of or all of the triblock copolymers can be photopolymerized as desired, which can be limited by the amount of photoinitiator used, the duration of photocrosslinking reaction, or other means. In some embodiments, the photocrosslinking reaction proceeds for 1 week or less, for 24 hours or less, for 12 hours or less, for 6 hours or less, for 2 hours or less, for 1 hour or less, for 30 minutes or less, for 10 minutes or less, for 5 minutes or less, or for 2 minutes or less.

Methods for Printing Articles

Also disclosed are methods of printing a three-dimensional (3D) article comprising: a) extruding a printing composition from a deposition nozzle moving relative to a substrate, the printing composition comprising a photoinitiator and a triblock copolymer having a formula A-B-A, wherein A is a polycaprolactone (PCL) block or a polyvalerolactone (PVL) block, B is a polyethylene glycol (PEG) block, and wherein the triblock copolymer comprises one or more ethylenically unsaturated moieties; b) depositing one or more layers comprising the printing composition on the substrate; and c) photocrosslinking the triblock copolymer to form the printed 3D article.

The various hydrogel compositions and methods to make hydrogels disclosed herein can be used in the methods for printing a 3D article. The printing compositions comprising a photo-crosslinkable triblock copolymer are useful as "inks" for three-dimensional (3D) printing (also known as direct-write printing) in printers utilizing an extrusion printhead. 3D printing refers to an additive deposition process for constructing three-dimensional single or multi-layered structures disposed on a substrate without using lithography. The features of the structures are defined by computer-aided design/computer-aided manufacturing (CAD/CAM) software. Devices for printing 3D articles are known, such as those disclosed in US Patent Application Publications US20180021140A1 and US20170217091A1, which are each incorporated by reference herein in their entireties.

The substrate can be any suitable base material (e.g., flexible film base, glass plate, metal foil, and the like), and can comprise one or more layers. The surface of substrate can have a temperature which is about the same as the temperature of the printing composition, or can alternatively be higher or lower to induce changes in efficiency of the crosslinking reaction.

The printing composition is extruded from a deposition nozzle moving relative to the substrate. The movement facilitates formation of single and/or complex shapes of the resultant printed article. The construction of the 3D layered structures is computer controlled and can be done in a laminar fashion. In one configuration, the deposition nozzle (e.g., of the printer) moves in the z direction and the substrate supporting the extruded printing composition moves in the x and y directions. In another configuration, the deposition nozzle moves in 3 dimensions and the substrate is stationary. In another configuration, the substrate moves in 3 dimensions and the deposition nozzle is stationary. The deposition nozzle can dispense continuously to generate microstrands of the printing composition, or discontinuously to dispense microdrops of the printing composition. Liquid flow of the printing composition can be controlled by air pressure (pneumatic nozzle) or using a stepper motor (volume-driven injection), or by other known methods. The strand thickness of the exuded printing composition can be modulated by varying the deposition speed, tip diameter, and/or the applied pressure. Strand thickness or the line width can also be a function of viscosity of the printing composition and interaction of hydrogel with the substrate.

The printing composition can be deposited onto the substrate, results in a simple or complex shape or structure disposed on the substrate. 3D printing facilitates the formation of virtually limitless shapes and structures, which can be used to mold structures used to mimic in vivo cell growth environments. In some embodiments, the one or more layers are deposited in a predetermined pattern. Resultant shapes/structures can be separated from the underlying substrate as a free-standing shape or structure if desired. Optionally, the extrusion and deposition steps can be repeated one or more times, applying the same or a different printing composition, each time in contact with or separate from (e.g., for later joining with) a previously deposited layer. Thus, complex structures comprising one or more layers, or one or more printing compositions, can be deposited on the substrate.

In some embodiments, any one or more steps of the 3D printing method can be performed at a temperature from about 1° C. to about 99° C., or from about 10° C. to about 75° C., or from about 20° C. to about 50° C., or from about 25° C. to about 37° C. In some embodiments, all steps of the 3D printing method can be performed at a substantially constant temperature (e.g., no temperature change is required).

The triblock copolymer is photocrosslinked to form the printed 3D article. In some embodiments, the photocrosslinking reaction is a free radical crosslinking reaction. The photocrosslinking step can be performed after the extrusion and deposition steps. Alternatively, the photocrosslinking step can be performed concurrent with one or more of the extrusion and deposition steps. For example, the photocrosslinking step can occur while the printing composition is being extruded, or while the printing composition is being deposited, or throughout the extrusion and deposition steps, and can continue to proceed thereafter.

In some embodiments, the printing composition further comprises one or more viable cells. In some embodiments, the printed 3D article is a scaffold for depositing and/or growing cellular tissue. A scaffold for cellular growth can have any suitable three-dimensional shape or dimensions. As a non-limiting example, a scaffold can comprise a stack of alternating layers of strands comprising the printing composition, wherein the layers of strands can be subjected to one or more mechanical stressors.

In some embodiments, the printing composition comprises from about $1 \times 10^1$ to about $1 \times 10^9$ viable cells, or from about $1 \times 10^2$ to about $1 \times 10^8$ viable cells, or from about $1 \times 10^3$ to about $1 \times 10^7$ viable cells, or from about $1 \times 10^4$ to about $1 \times 10^7$ viable cells, or from about $1 \times 10^5$ to about $1 \times 10^7$ viable cells.

In some embodiments, the methods can further comprise culturing the one or more viable cells after the photocrosslinking step. Standard cell culture techniques are typically used. In embodiments in which the printing composition comprises one or more cells and is 3D printed into a printed article, subsequent addition of cells is not required but also not restricted. In such embodiments, a portion of or the entire printed article can be placed under standard cell culture conditions (e.g., temperature, pressure, nutrient concentrations, etc.).

Viable cells include prokaryotic and eukaryotic cells. Non-limiting examples of eukaryotic cells include mammalian cells (e.g., stem cells, progenitor cells and differentiated cells). Stem cells have the ability to replicate through numerous population doublings (e.g., at least 60-80), in some cases essentially indefinitely, and also have the ability to differentiate into multiple cell types (e.g., pluripotent or multipotent). Other viable cells include immortalized cells that do not undergo normal replicative senescence, and can proliferate essentially indefinitely. Other living cells include embryonic stem cells, amniotic fluid stem cells, cartilage cells, bone cells, muscle cells, skin cells, pancreatic cells, kidney cells, nerve cells, liver cells, and the like. Viable cells are living cells.

The printing composition can comprise a viable cell in an encapsulated form. Encapsulated cells are cells or small clusters of cells or tissue that are surrounded by a selective membrane laminate that allows passage of oxygen and other required metabolites, releases certain cell secretions (e.g., insulin), but limits the transport of the larger agents of the host's immune system to prevent immune rejection. Encapsulation can be useful for implanting and/or injecting cells or tissues containing living xenogeneic or allogeneic cells while reducing the risk of immune rejection in a host. This can be useful in treating diseases due to inadequate or loss or secretory cell function, or ailments that would benefit from the addition of certain secretory cells such as acute liver failure, type I diabetes, chronic pain, Parkinson's disease, and other diseases. Other uses of encapsulated cells include, but are not limited to, single cell analysis, high throughput drug screening, and stem cell differentiation at the single cell level. The cells can be encapsulated in a microcapsule of from 50 or 100 micrometers to 1 or 2 mm in diameter. The microcapsules can include one or more living cells, preferably 1 to 10 living cells, more preferably 1 to 5 living cells.

The printed 3D article, preferably a printed 3D article comprising one or more viable cells, can be subjected to one or more mechanical stressors. For example, the printed 3D article comprising one or more viable cells can be placed in standard cell culture conditions and further subjected to one or more mechanical stressors to mimic in vivo conditions. Mechanical stressors include twisting, bending, compressing, stretching, tension, pressure, and the like. The mechanical stressors can be applied continuously, transiently, or discontinuously (e.g., in a regular or irregular pulsating manner to mimic blood flow and pressure).

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Figure 7A:
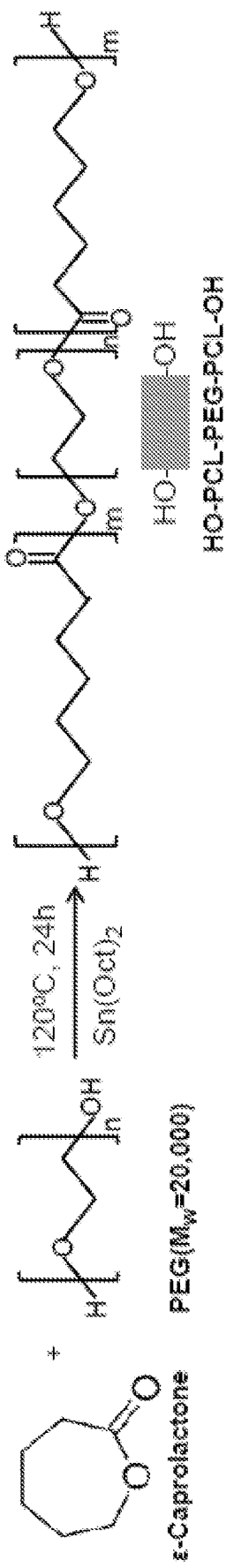
FIGS. 7A through 7C show synthetic schemes of PCL-PEG-PCL copolymer diols via ring-opening polymerization (FIG. 7A), and acrylated PEG-PCL-DA and PEG-DA polymers (FIG. 7B).
Figure 7B:
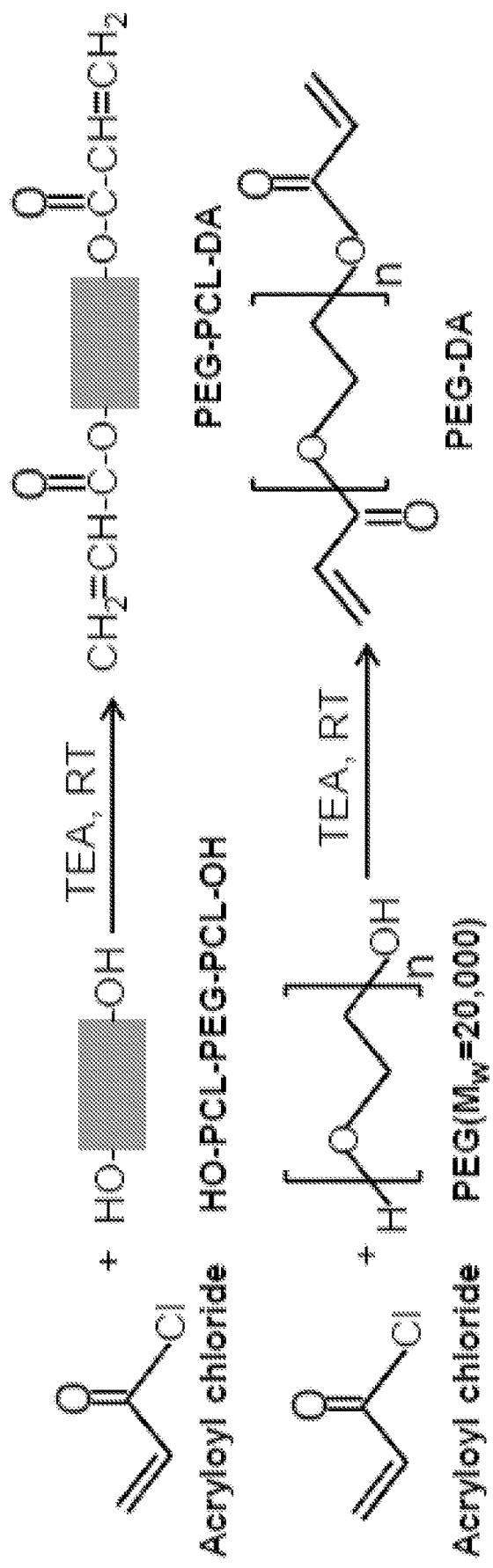
Figure 7C:
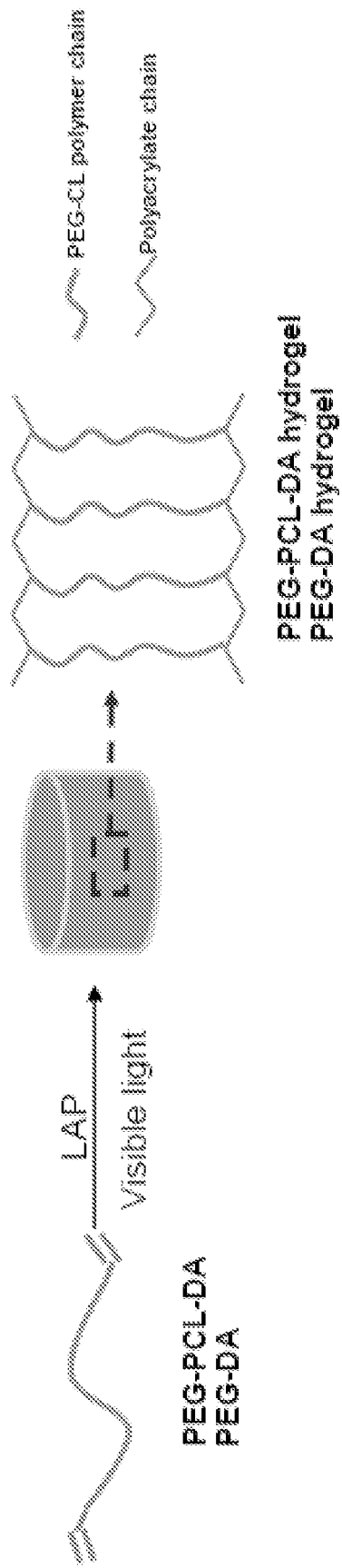

Material and Methods
  Materials.
  Polyethylene glycol (PEG, MW=20,000, Sigma) and ε-caprolactone (CL, Sigma) were dried in a vacuum oven at 60° C. to remove residual water before use. Stannous octoate ($Sn(Oct)_2$, Sigma), triethylamine (TEA, Sigma), acryloyl chloride (Sigma), dichloromethane (Sigma), dimethyl phenylphosphonite (Acros Organics), 2,4,6-trimethylbenzoyl chloride (Sigma), lithium bromide (Sigma), and 2-butanone (Sigma) were used as received.
  Synthesis of PCL-PEG-PCL Copolymer Diols.
  PCL-PEG-PCL diols were synthesized using PEG to initiate a ring opening polymerization of CL at 120° C. for 24 h under $N_2$ atmosphere (FIG. 7A).[24] $Sn(Oct)_2$ was used as a catalyst. Reaction products were dissolved in dichloromethane and precipitated in cold diethyl ether, then dried in a vacuum oven at 60° C. for 3 days.
  Acrylation of PCL-PEG-PCL Copolymer Diols.
  Acrylation of the PCL-PEG-PCL copolymer diols was achieved using acryloyl chloride (FIG. 7B). Copolymer diols were dissolved in 15 mL dichloromethane in a 3-neck flask under $N_2$ protection, to which TEA was added dropwise under stirring for 30 min in an ice bath.[25] Acryloyl chloride in 15 mL of dichloromethane was then added to the mixture dropwise. The molar ratio of the hydroxyl groups (—OH) in PCL-PEG-PCL diols:TEA:acryloyl chloride was 1:2:2. The reaction was first performed in the ice bath for 30 min, then heated to 40° C. for 24 h under $N_2$ atmosphere. The reaction mixture was cooled to room temperature, then precipitated in cold diethyl ether. Precipitates were filtered, dried in a desiccator for 2 days, then re-dissolved in deionized water and dialyzed for 2 days. Synthesized PEG-PCL-DA was collected after lyophilization. The PEG-PCL-DA polymers were set as PEG-PCL(X)-DA, X referring to the block length of the PCL-PEG-PCL diols. PEG-DA without PCL segments served as a control, which was synthesized from PEG (MW=20,000) and acryloyl chloride via the same reaction process as described above.
  Proton Nuclear Magnetic Resonance ($^1$H NMR) Spectroscopy.
  The chemical structures of the PEG-PCL-DA and PEG-DA polymers were characterized by $^1$H NMR (JEOL ECX instrument, 300 MHz) with $D_2O$ as a solvent. The block length of the PCL-PEG-PCL copolymer diols and the degree of substitution (DS) of the acryloyl group on both ends of the PCL-PEG-PCL diols were both calculated from the $^1$H NMR spectra.
  Elastic Hydrogel Formation.
  PEG-PCL-DA hydrogel was formed by photopolymerization using lithium phenyl(2,4,6-trimethylbenzoyl) phosphinate (LAP) as the water-soluble, visible light initiator. LAP was synthesized according to previous studies (FIG. 7C).[26,27] PEG-PCL-DA polymers were dissolved in deionized water and mixed with aqueous LAP solution to reach various final concentrations (10%, 20% and 40% wt/v). Mixed solution were then poured into a cylinder or strip mold, followed by exposure under a LED splash lighter (395-405 nm, 5 W) for 2 min to irradiate the mixed solutions. Then, the PEG-PCL-DA hydrogels were formed. Unless otherwise noted, the hydrogels used for all measurements were at a concentration of 40%.
  Hydrogel Water Absorption.
  To determine the swelling ratio of PEG-PCL-DA hydrogels, the cylinder samples (4 mm in height, 9 mm in diameter; n=3) were immersed in PBS at 37° C. for 24 h.[28] Hydrogels were then removed and the surface water of the hydrogels was removed gently with a filter paper, and the hydrogels were weighed ($W_s$). Swollen hydrogels were rinsed by deionized water and lyophilized. The weight of dry hydrogels after freeze-drying was recorded as $W_d$. The swelling ratio was calculated as $(W_s-W_d)/W_d \times 100\%$.
  Mechanical Property Measurements.
  Hydrogels used for all mechanical measurements were in wet state (immersion in PBS for 24 h) before testing. Compression testing of cylinder hydrogels (4 mm in height, 9 mm in diameter; n=4) was performed on MTS Insight testing system with a 10 N load cell and a cross head rate of 1 mm/min.[29] For uniaxial tensile testing, strips of PEG-PCL-DA hydrogels 50 mm in length, 5 mm in width, and 3 mm in height (n=3) were prepared and tested on MTS Insight Testing System with a 500 N load cell and a cross head rate of 10 mm/min according to ASTM D638-03.[30] The instant strain recovery of PEG-PCL-DA hydrogel strips (n=4) were prepared and measured under the same conditions as described above.[31] The hydrogel strip was stretched to 10% strain, held for 1 min, and then released. The stretching cycle was repeated 3 times. The original length ($L_0$) and the length after stretching ($L_1$) were measured by a caliper. The instant strain recovery was calculated as $(1-(L_1-L_0)/L_0) \times 100\%$. For cyclic stretch, PEG-PCL-DA hydrogel specimens (50 mm in length, 5 mm in width, 3 mm in height; n=3) were stretched to the maximum strain of 30%, and released back to 0% strain for 10 cycles at a constant rate of 10 mm/min.[32]
  Cell Viability in Hydrogels.
  PEG-PCL-DA polymers (1.2 g) and LAP (0.015 g) were sterilized under UV radiation for 1 h and dissolved in 1 mL sterilized PBS to obtain 120% (wt/v) PEG-PCL-DA/PBS solution, and 1.5% (wt/v) LAP/PBS solution, respectively. Mouse 3T3 fibroblasts (ATCC, Manassas, VA) in 1 mL cell culture medium (DMEM supplemented with 10% fetal bovine serum, 100 U/mL penicillin, and 100 μg/mL streptomycin) at a density of $1.5 \times 10^7$ cells/mL was first mixed with PEG-PCL-DA/PB S solution, then subsequently blended with LAP/PBS solution. The final PEG-PCL-DA hydrogel concentration was 40% (wt/v), the final initiator concentration was 0.5% (wt/v) and the final cell density in the obtained cell/hydrogel precursor was $5 \times 10^6$ cells/mL. The cell/hydrogel precursor was injected into a mold by a 1 mL syringe and exposed to a LED splash lighter to form a cell/hydrogel construct. Standard biopsy punches (6 mm, Miltex) were used to punch the cell/hydrogel construct to obtain cell/hydrogel disks (6 mm diameter), which were transferred to 24-well cell culture plates and incubated at 37° C. in a 5% $CO_2$ environment. The cell culture medium was exchanged every 2 days. Cell viability after 1 and 3 days of incubation in PEG-PCL-DA hydrogels (n=5) was detected by a mitochondrial activity assay (MTT, Sigma) at 1 and 3 days. MTT results were verified using a live & dead staining kit (live, SYTO 10 green fluorescent nucleic acid stain; dead, ethidium homodimer-1 nucleic acid stain, Life Technologies, Inc.) to visualize 3T3 fibroblasts in hydrogels. Images of live/dead stained 3T3 fibroblasts were taken on a fluorescence microscope.

Viscosity of PEG-PCL-DA Solution.

PEG-PCL-DA polymers were dissolved in PBS to create solutions ranging from 10-40% (wt/v). The viscosity of the polymer solutions was measured using a falling ball viscometer (size 3, Gilmont) under manufacturer's instructions. A glass ball was used to measure the viscosity of polymer solutions that were less than 10% (wt/v) and a stainless-steel ball was used for the other concentrations. Three measurements were taken for each concentration. Shear stress within the nozzle during bioprinting is estimated using the Hagen-Poiseuille equation:

$$\tau = 32 \cdot \mu \cdot \frac{Q}{\pi \cdot d^3},$$

where $\mu$ is the viscosity, Q is the mean volumetric flow rate and d is the diameter of the needle.

Cell Printing of PEG-PCL-DA.

All cell printing experiments were performed using a modified printing platform reported in previous studies.[8] The printer contained a dispenser mounted onto a Cartesian robotic stage that moved in the x-y direction. Another motor-controlled stage that moves in the z-direction, acted as the printing substrate. The extrusion-based dispenser was driven by a syringe pump (Harvard Apparatus); the speed of extrusion was controlled by programming the pump. Printing resolution was controlled by adjusting the speed of extruder movement, extrusion speed and nozzle size. Syringe barrels containing the bioink and tubing attached to the dispenser were covered in aluminum foil to prevent premature cross-linking during the printing process. The printing apparatus was housed in a sterile laminar flow hood to prevent contamination. Basic geometric shapes were printed by extruding a 20% (wt/v) PEG-PCL-DA solution through an 18 G needle and a 21 G needle.

Cell Viability Under Printing Conditions.

Sterilized PEG-PCL-DA polymers of varying weight (0.1-0.3 g) were dissolved in 500 µL of media to obtain polymer/medium solutions. Three types of media were used: fibroblast growth medium (FGM-2, Lonza) for neonatal human lung fibroblasts, endothelial growth medium (EGM-2, Lonza) for human umbilical vein endothelial cells and smooth muscle growth medium (SmGM-2, Lonza) for human aortic smooth muscle cells. The cells were suspended in their respective media at a concentration of $2.5 \times 10^6$ cells/mL. 400 µL of the cell suspension were mixed with polymer solution, then subsequently mixed with 100 µL of LAP/PBS solution to obtain a PEG-PCL-DA bioink with a final concentration of 10-30% (wt/v), final initiator concentration of 0.5% (wt/v) and a final cell density of $1.0 \times 10^6$ cells/mL. The resulting bioink was wrapped in aluminum foil and kept on ice prior to printing. The bioink was loaded into sterile 10 mL luer lock syringes (Becton Dickinson) and mounted onto a printing apparatus. The bioink was extruded through nozzles of four different gauges (18G, 21G, 23G and 25G) at a constant flow rate of 0.15 mL/min and photo-crosslinked for 30 seconds to create cylindrical cell/hydrogel constructs. Live/dead staining (live, calcein AM; dead, ethidium homodimer-1, ThermoFisher Scientific) was used to determine cell viability of cells immediately after printing (n=3). The constructs were immersed in media and incubated under 37° C. in a 5% $CO_2$ environment. Media was changed every 2 days and live/dead staining was performed again 7 days after printing.

Statistical Analysis.

All results are presented as mean±standard deviation. All data were analyzed by one-way ANOVA followed by a post hoc Tukey-Kramer test. Differences were considered statistically significant when $p < 0.05$.

Results and Discussion

PEG-PCL-DA Polymer Synthesis and Hydrogel Formation.

FIG. 1 describes the triblock copolymer arrangement and its use in forming a bio-printable, biodegradable, single-component hydrogel which possesses good mechanical properties to support cell culture applications. The left panel of FIG. 1 describes one embodied arrangement of polymeric blocks in the copolymer, which are acrylated at termini and cross-linked via a visible light-responsive photoinitiator. The middle panel of FIG. 1 describes several desirable mechanical properties for cell culturing hydrogels, including desirable stretching, compression, and twisting properties. The right panel of FIG. 1 describes an embodiment in which viable cells are combined with the hydrogel matrix, 3D printed into a complex shape, and are subjected to polymerization stimuli without compromising the integrity of the cells embedded in the hydrogel matrix.

Figure 2A:
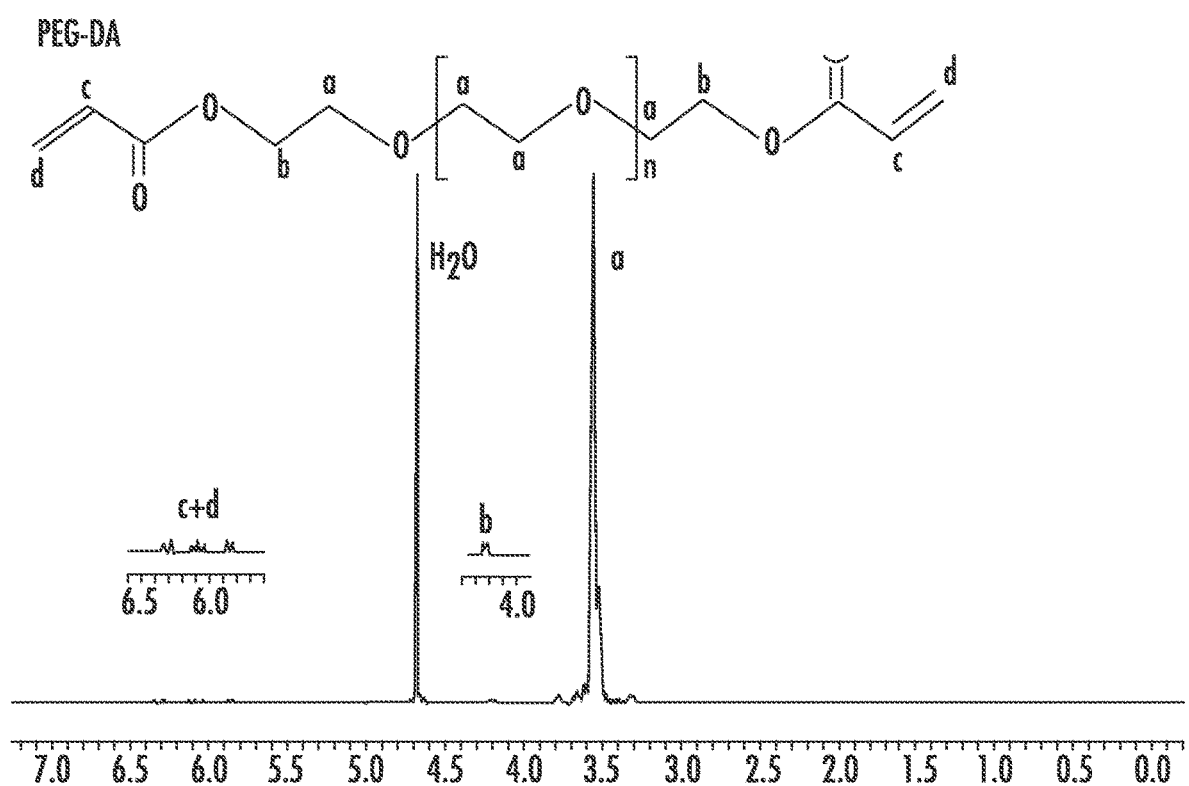
FIGS. 2A through 2B show the polymeric formula and the $^1$H-NMR spectra of PEG-DA (FIG. 2A) and PEG-PCL (24K)-DA (FIG. 2B).
Figure 2B:
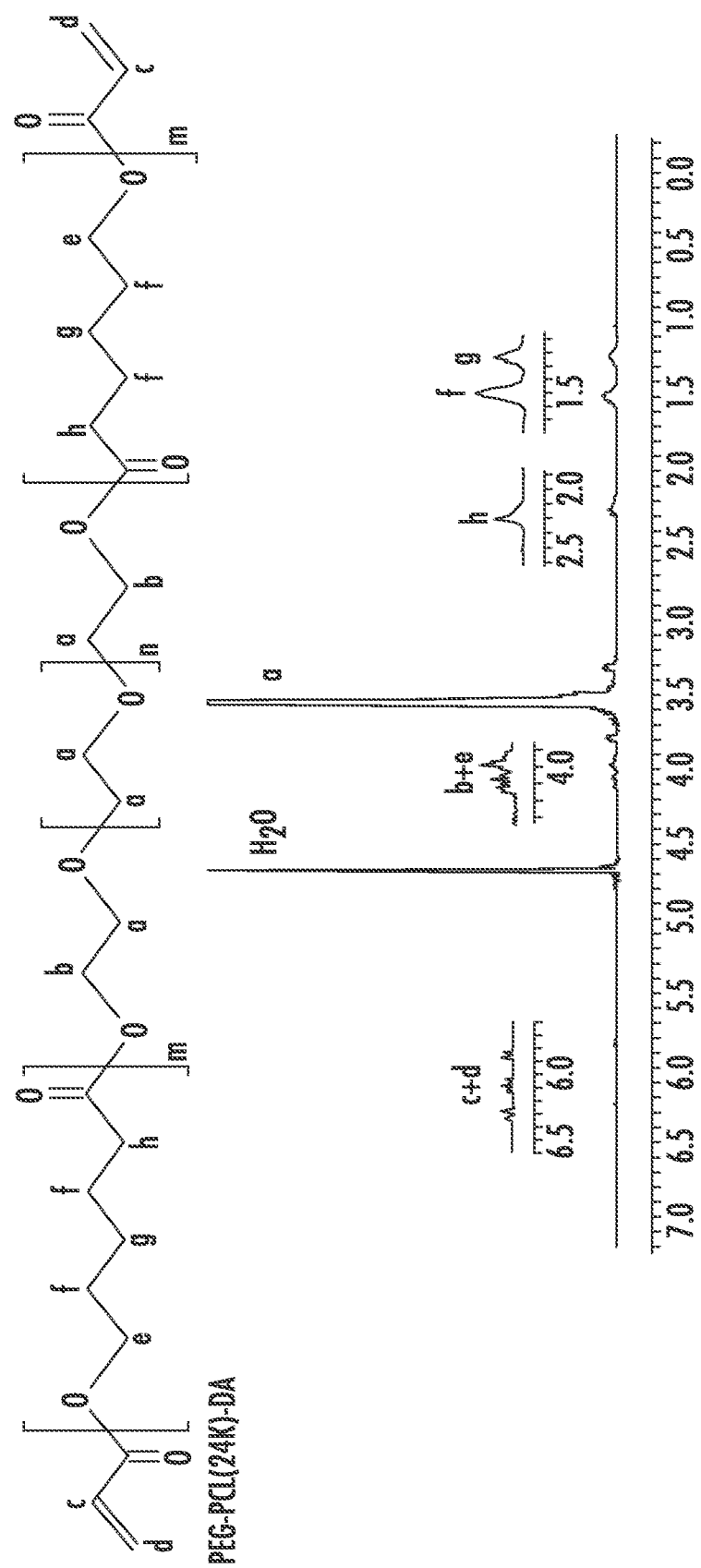

The chemical structure of synthesized PEG-DA control (FIG. 2A) and PEG-PCL-DA (FIG. 2B) were confirmed by $^1$H-NMR spectra. The specific peaks of the ethylene oxide protons of the PEG segments in PEG-DA and PEG-PCL-DA polymers were located at 3.55 and 4.20 ppm, and 3.56 and 4.09 ppm, respectively (FIGS. 2A and 2B). The methyl protons of the PCL blocks in the PEG-PCL-DA polymer were assigned to chemical shifts between 1.22 and 3.99 ppm (FIG. 2B). The specific peaks of the acryloyl protons in PEG-PCL-DA were located from 5.81 to 6.30 ppm (FIG. 2B). The block length of the PCL-PEG-PCL was calculated from the $^1$H NMR spectra and distributed as 1863-20000-1863 for PEG-PCL(24K) and 1151-20000-1151 for PEG-PCL(22K) (Table 1). The degree of substitution (DS) of the acryloyl group calculated from $^1$H NMR was 55%, 59% and 60% for PEG-DA, PEG-PCL(22K)-DA and PEG-PCL (24K)-DA, respectively. The DS of the acryloyl group for PEG-DA is comparable to previous reports[33], verifying successful acrylation.

TABLE 1

Block lengths of PCL-PEG-PCL copolymer diols

| Copolymer diols | Theoretical block length of PCL-PEG-PCL | Calculated block length of PCL-PEG-PCL |
|---|---|---|
| PEG-PCL(24K) | 2000-20000-2000 | 1863-20000-1863 |
| PEG-PCL(22K) | 1000-20000-1000 | 1151-20000-1151 |

The hydrogel was formed by covalent crosslinking via visible light initiation. The formed hydrogel was transparent.

The triblock PCL/PEG system previously was designed for thermal-sensitive biodegradable hydrogel, which depended on the hydrophobicity/hydrophilicity balance by changing the feeding ratio of PEG/PCL and total macromolecular weight. The thermo-sensitive PEG/PCL hydrogel was opaque and not elastic.[34-36] In contrast, the acrylated PEG/PCL polymer disclosed herein can form transparent and elastic hydrogel via photopolymerization under exposure to visible light. The selected photoinitiator, lithium phenyl(2,4,6-trimethylbenzoyl) phosphinate (LAP), can maintain high cell viability during direct cellular encapsulation because it has very good cell compatibility in vitro and in vivo,[26, 37] and can trigger photo-polymerization under visible light (395-405 nm) exposure.[26] Visible light for cross-linking is much safer than the common UV crosslinking (365 nm), and facilitates safer and longer duration of cell printing. In addition, light crosslinking technique is highly compatible with current 3D printing technique.

Hydrogel Water Absorption.

Water absorption of PEG-PCL-DA hydrogel is summarized in Table 2. A decrease in water absorption was observed with an increase in the concentration of PEG-PCL-DA precursor solution. The water absorption of PEG-PCL(24K)-DA-10% was 1930±140%; however, this decreased to 766±18% when the concentration of PEG-PCL(24K)-DA precursor solution increased to 40% (Table 2). This was likely due to more polymer chains involved in the cross-linking process, thereby resulting in a denser hydrogel mesh, and thus a lower water absorption rate.[38]

TABLE 2

PEG-PCL-DA hydrogel characterization*,#

| Polymers/Concentrations | | Compressive modulus (kPa) | Compressive stress at 80% strain (kPa) | Water absorption (%) |
|---|---|---|---|---|
| PEG-PCL(24K)-DA | 40% | 26.7 ± 4.5$^a$ | 356.8 ± 18.7$^a$ | 766 ± 18$^a$ |
| | 20% | 14.9 ± 3.1$^b$ | 162.5 ± 14.5$^b$ | 1184 ± 43$^b$ |
| | 10% | 10.7 ± 2.5$^b$ | 78.6 ± 4.5$^c$ | 1930 ± 140$^c$ |
| PEG-PCL(22K)-DA | 40% | 19.4 ± 1.5$^a$ | —## | 971 ± 48$^a$ |
| | 20% | 8.9 ± 1.7$^b$ | 122.4 ± 2.3$^a$ | 1593 ± 51$^b$ |
| | 10% | 4.9 ± 0.4$^c$ | 45.0 ± 5.2$^b$ | 2504 ± 337$^c$ |
| PEG-DA | 40% | 9.2 ± 1.8$^a$ | —## | 1692 ± 296$^a$ |
| | 20% | 4.7 ± 0.5$^b$ | 24.1 ± 2.7$^a$ | 2819 ± 292$^b$ |
| | 10% | 1.1 ± 0.2$^c$ | 8.8 ± 1.8$^b$ | 3798 ± 276$^c$ |

*$^{a,b,c}$represent significantly different groups for each characteristic.
The compression testing of hydrogels was carried out after immersion in PBS for 24 h.
The PEG-DA and PEG-PCL(22K)-DA hydrogels at 40% concentration were broken at 80% strain during the compressive test.

Incorporation of hydrophobic PCL segments into the network resulted in a decreased water absorption rate. The PEG-DA without PCL segments had the highest water absorption rate at 1692±296%. The PEG-PCL(24K)-DA with the highest PCL content had the lowest water absorption rate at 766±18%. A balance exists between water absorption from the hydrophilic PEG moiety and the enhanced mechanical properties and elasticity primarily attributed to the hydrophobic PCL moiety.

It is important to characterize water absorption to predict the swollen shape and size for a bioprinted construct,[39] and to be optimal for cell culture. But the range of water adsorption appropriate for both printing and cell survival is not well defined. Others reported that materials with water absorption from 78% (PEG-alginate hydrogel) to 1183% (GelMA/Collagen hydrogel) were acceptable for printing.[20, 40-42] However, optimal hydrogel water absorption rates for printing and cell growth are often opposing.[43, 44] No strong evidence shows that such water absorption ranges were good for cell culture. The water absorption rates reported herein for PEG-PCL(24K)-DA hydrogel (766%-1930%) are comparable to reported acceptable printable ranges (78%-1183%). In addition, introducing a low molecular weight cross-linker or a polymer with low water absorption can assist in reducing the water absorption rate of the PEG-PCL-DA hydrogel.[42, 45, 46]

Mechanical Properties of PEG-PCL-DA Hydrogel.

Figures 3A, 3B, 3C, 3D, 3E, 3F:
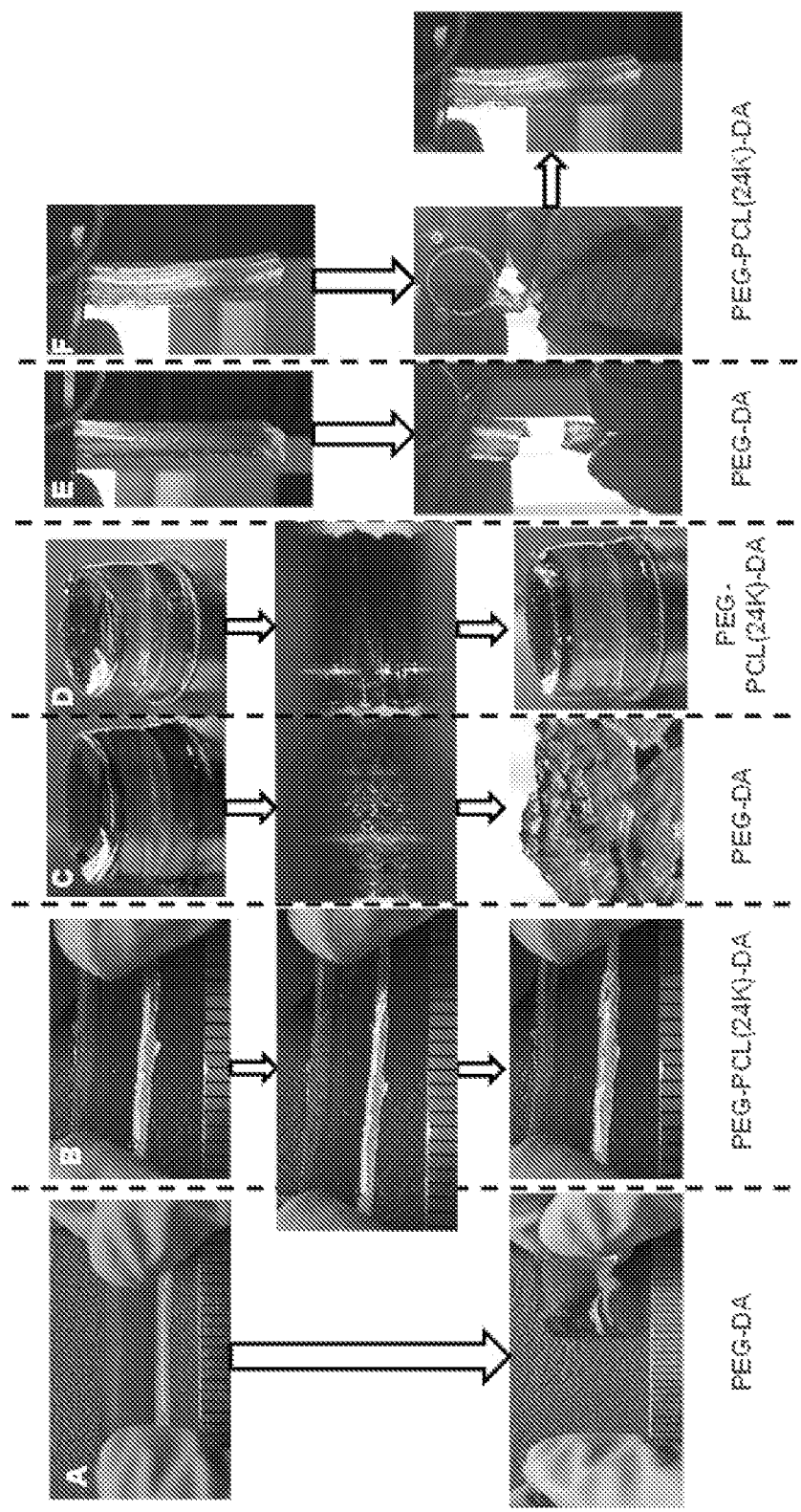
FIGS. 3A through 3F are images demonstrating the attractive mechanical properties of the PEG-PCL(24K)-DA hydrogel under stretching, compression and twisting. PEG-DA hydrogel broke under stretching (FIG. 3A). PEG-PCL (24K)-DA hydrogel was stretched and recoiled back to the original length (FIG. 3B). PEG-DA hydrogel broke into pieces under compression at 80% strain (FIG. 3C). PEG-PCL(24K)-DA hydrogel deformed and recovered under compression (FIG. 3D). PEG-DA hydrogel broke after twisting for 4 cycles (FIG. 3E). PEG-PCL(24K)-DA hydrogel was twisted for 4 cycles and recovered after releasing (FIG. 3F).

The hydrogel desirably should maintain elasticity under media culture condition (wet state). Thus, hydrogel mechanical properties were examined after submerging the hydrogel in media overnight. PEG-PCL(24K)-DA hydrogel exhibited high flexibility and elasticity by withstanding large deformations of stretching (FIG. 3B), compression (FIG. 3D) and twisting (FIG. 3F) without obvious breakage. After removal of the applied force, the PEG-PCL(24K)-DA hydrogel recovered quickly from deformation. In contrast, swollen PEG-DA hydrogel broke after slight stretching (FIG. 3A), large deformation of compression (FIG. 3C), and twisting (FIG. 3E). The brittle nature of PEG-DA hydrogel is consistent with previous studies reporting swollen PEG-DA hydrogel (Mn=20,000 g/mol) broke upon high deformation of compression or slight stretching.[33]

Figure 4A:
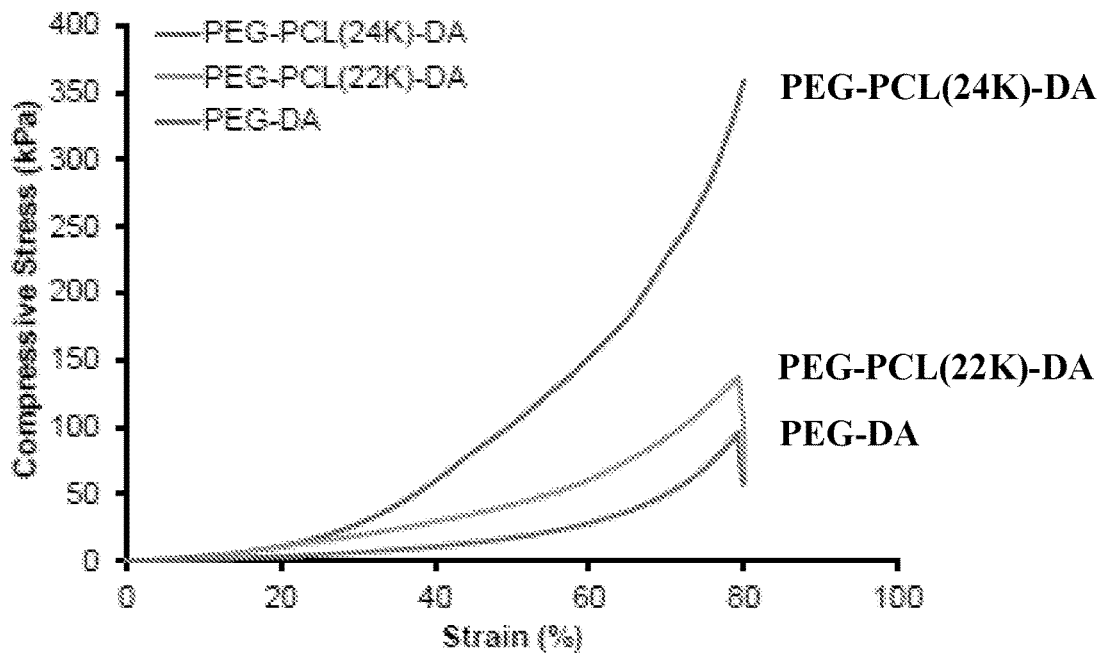
FIGS. 4A through 4C are graphs showing mechanical properties of PEG-PCL(24K)-DA hydrogel.
Figure 8A:
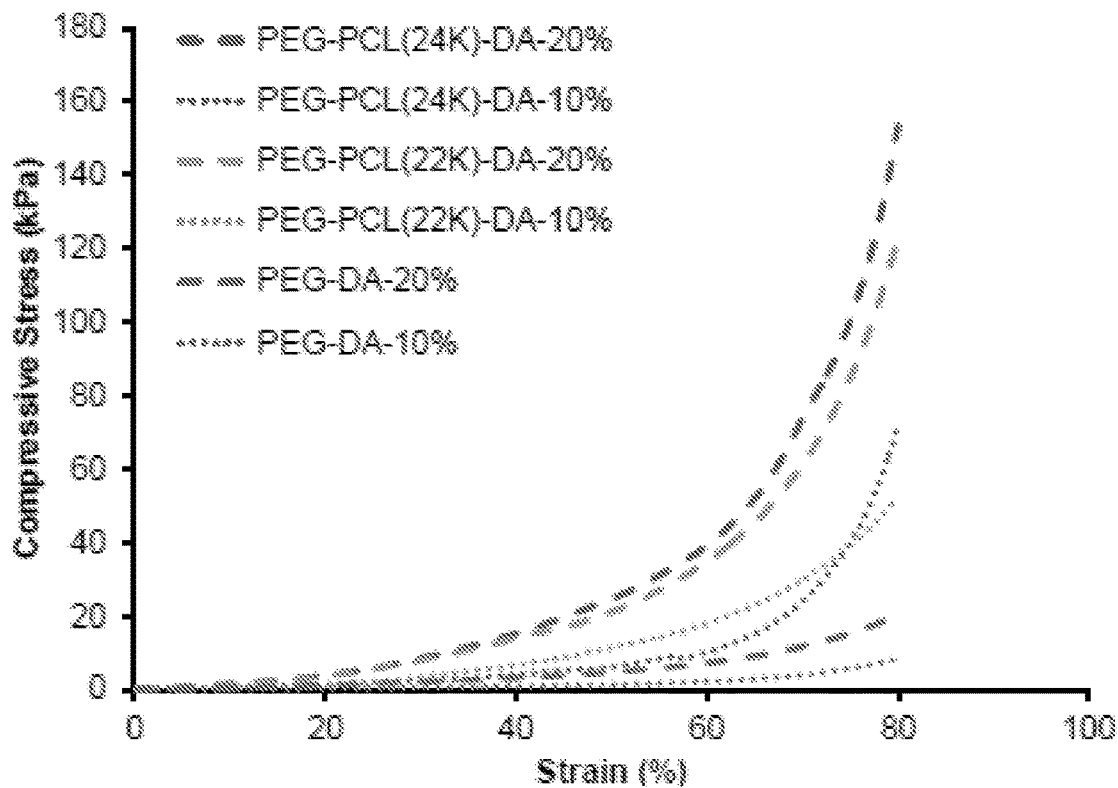
FIGS. 8A through 8B are graphs showing a comparison of compression (FIG. 8A) and tensile properties (FIG. 8B) of PEG-PCL-DA hydrogels at 10% and 20% concentrations after 24 h PBS immersion (wet state).

As determined by compressive testing (FIG. 4A, FIG. 8A and Table 2), the initial modulus and compressive strength at 80% strain of PEG-PCL-DA hydrogels increased with increasing PCL segments when the polymer concentration was fixed (p<0.05). PEG-PCL(24K)-DA hydrogel achieved a compressive stress of 356.8±18.7 kPa and a compressive modulus of 26.7±4.5 kPa at 80% strain, which was about three times higher than the compressive modulus of PEG-DA hydrogel (9.2±1.8 kPa). The compressive stress at 80% strain of PEG-DA could not be examined due to hydrogel collapse at 80% deformation.

Figure 4B:
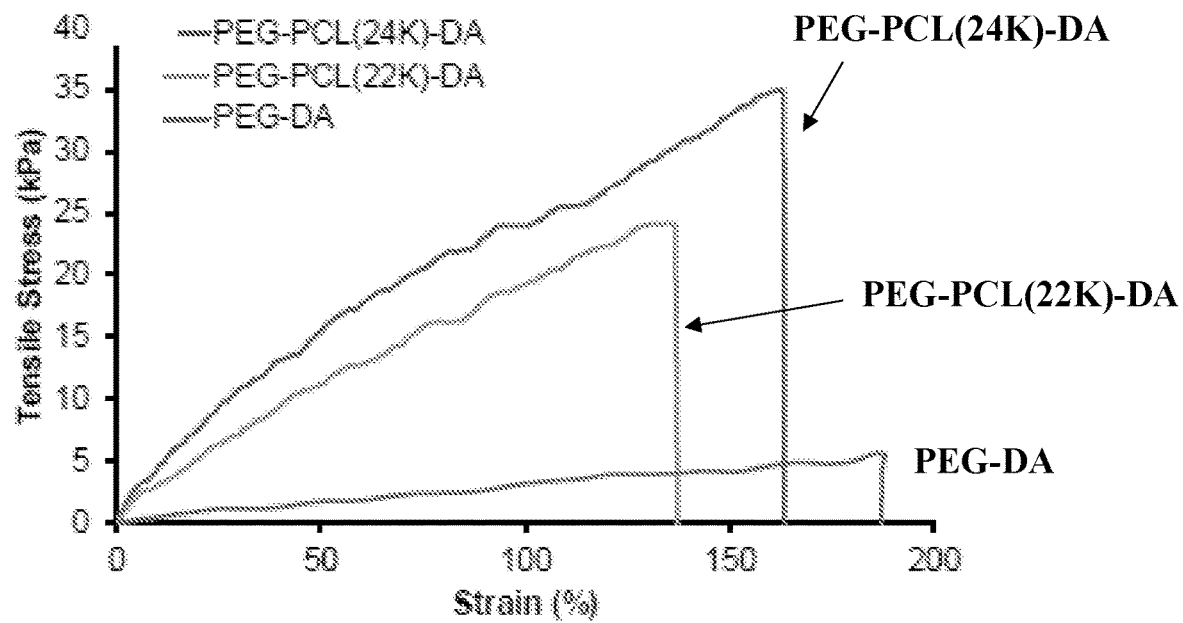
Figure 4C:
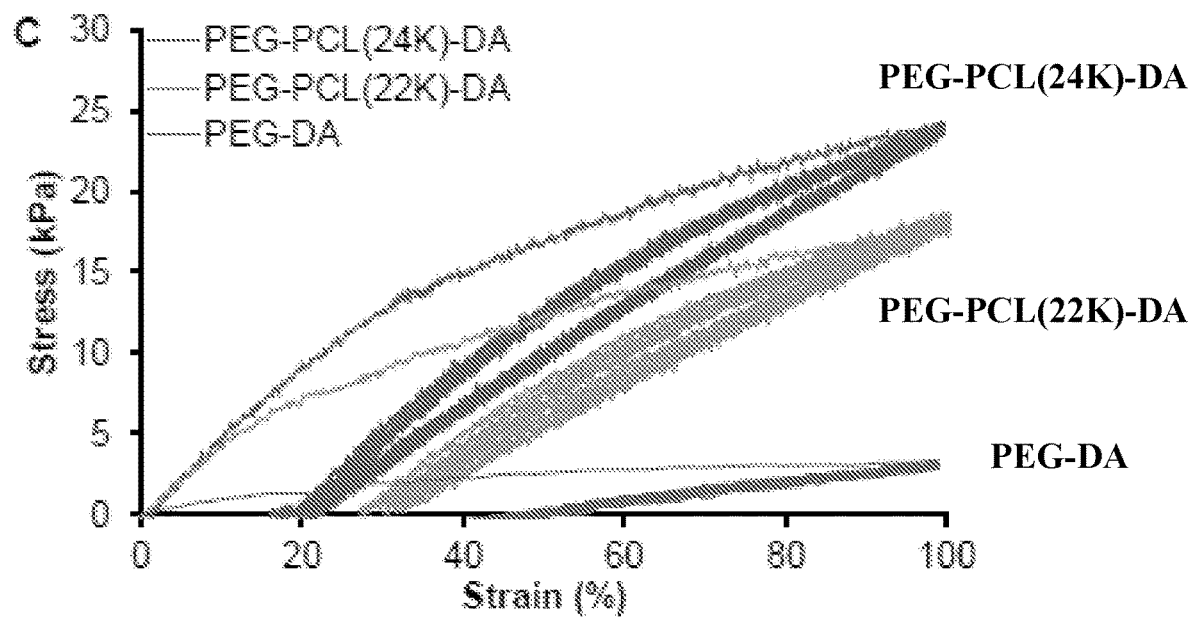
Figure 8B:
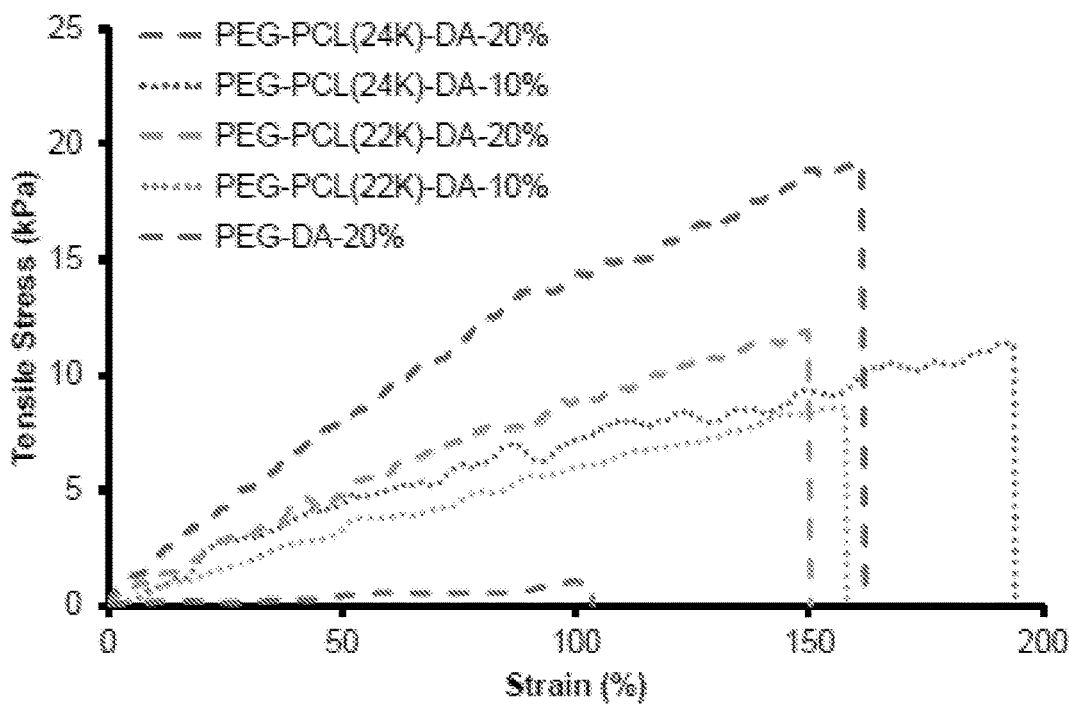

Tensile properties (FIG. 4B, FIG. 8B and Table 3) of PEG-PCL-DA hydrogels demonstrated trends similar to the compressive properties. The initial modulus and tensile stress of PEG-PCL(24K)-DA hydrogel were 37.7±1.7 kPa and 34.5±2.5 kPa, respectively, which were 6.3 times and 8.2 times higher than the initial modulus (6.0±1.2 kPa) and tensile stress (4.2±1.2 kPa) of PEG-DA, respectively. No significant difference was observed for the breaking strain between the PEG-PCL(24K)-DA (150±14%), PEG-PCL(22K)-DA (145±17%) and PEG-DA (187±27%) (p>0.05). The instant recovery of both PEG-PCL(22K)-DA and PEG-PCL(24K)-DA hydrogel was ≥99% for 3 cycles at 10% strain, which was larger than that of PEG-DA hydrogel (97±1%) (p<0.05; Table 3). PEG-PCL(24K)-DA hydrogel had the highest suture retention strength at 0.32±0.06 N/mm$^2$, while the PEG-DA had the lowest suture retention strength at 0.15±0.01 N/mm$^2$ (p<0.05; Table 3). Cyclic stretching was carried out to study the elasticity of the PEG-PCL-DA hydrogels at a maximum strain of 100% (FIG. 4C).

TABLE 3

Tensile testing of PEG-PCL-DA hydrogel*,#

| Polymers/Concentrations | | Initial modulus (kPa) | Tensile strength (kPa) | Breaking strain (%) | Suture retention (N/mm$^2$) | Instant recovery (%) |
|---|---|---|---|---|---|---|
| PEG-PCL(24K)-DA | 40% | 37.7 ± 1.7$^a$ | 34.5 ± 2.5$^a$ | 150 ± 14$^a$ | 0.32 ± 0.06$^a$ | 100 ± 1$^a$ |
| | 20% | 16.4 ± 4.8$^b$ | 18.7 ± 4.3$^b$ | 165 ± 25$^{a,\ b}$ | | |
| | 10% | 9.4 ± 1.9$^c$ | 10.8 ± 2.6$^c$ | 202 ± 27$^b$ | | |
| PEG-PCL(22K)-DA | 40% | 28.2 ± 2.4$^a$ | 25.3 ± 2.1$^a$ | 145 ± 17 | 0.20 ± 0.02$^b$ | 99 ± 1$^a$ |
| | 20% | 10.7 ± 1.3$^b$ | 12.3 ± 1.1$^b$ | 160 ± 12 | | |
| | 10% | 5.5 ± 0.6$^c$ | 8.6 ± 1.0$^c$ | 176 ± 21 | | |
| PEG-DA | 40% | 6.0 ± 1.2$^a$ | 4.2 ± 1.2$^a$ | 187 ± 27$^a$ | 0.15 ± 0.01$^c$ | 97 ± 1$^b$ |
| | 20% | 1.4 ± 0.3$^b$ | 1.2 ± 0.2$^b$ | 102 ± 15$^b$ | | |
| | 10% | —## | —## | —## | | |

*$^{a,b,c}$represent significantly different groups for each characteristic.
The tensile testing of hydrogels was carried out after immersion in PBS for 24 h. The suture retention and instant recovery were measured for hydrogels at a concentration of 40%.
The PEG-DA -10% hydrogel was too weak to be loaded on the MTS machine.

Figure 9A:
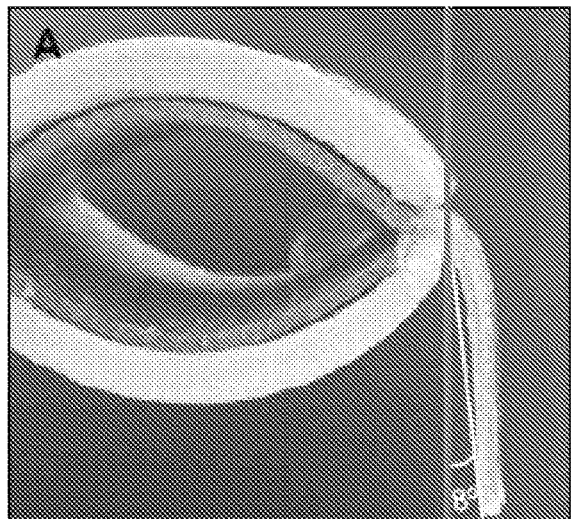
FIGS. 9A through 9C are images showing qualitative depictions of hydrogels suspended on a cantilever right after gelation of hydrogels PEG-DA (FIG. 9A), PEG-PCL(22K)-DA (FIG. 9B), and PEG-PCL(24K)-DA (FIG. 9C).
Figure 9B:
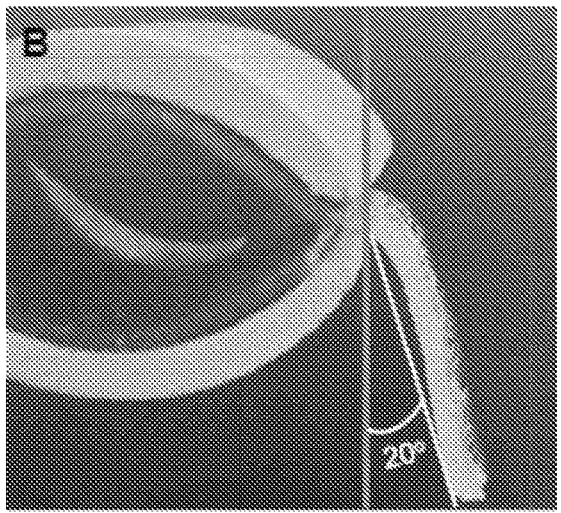
Figure 9C:
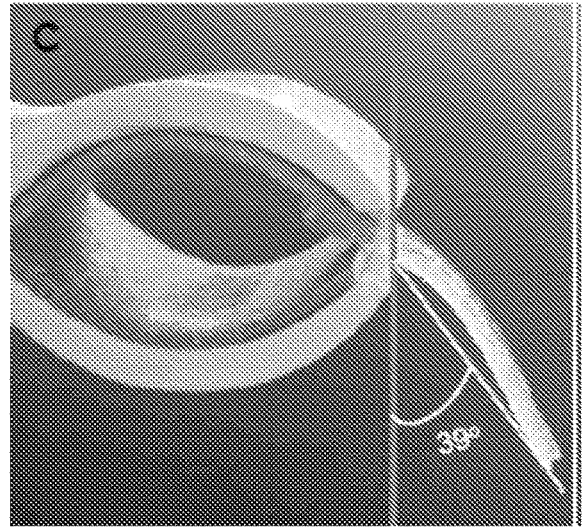
Figure 10:
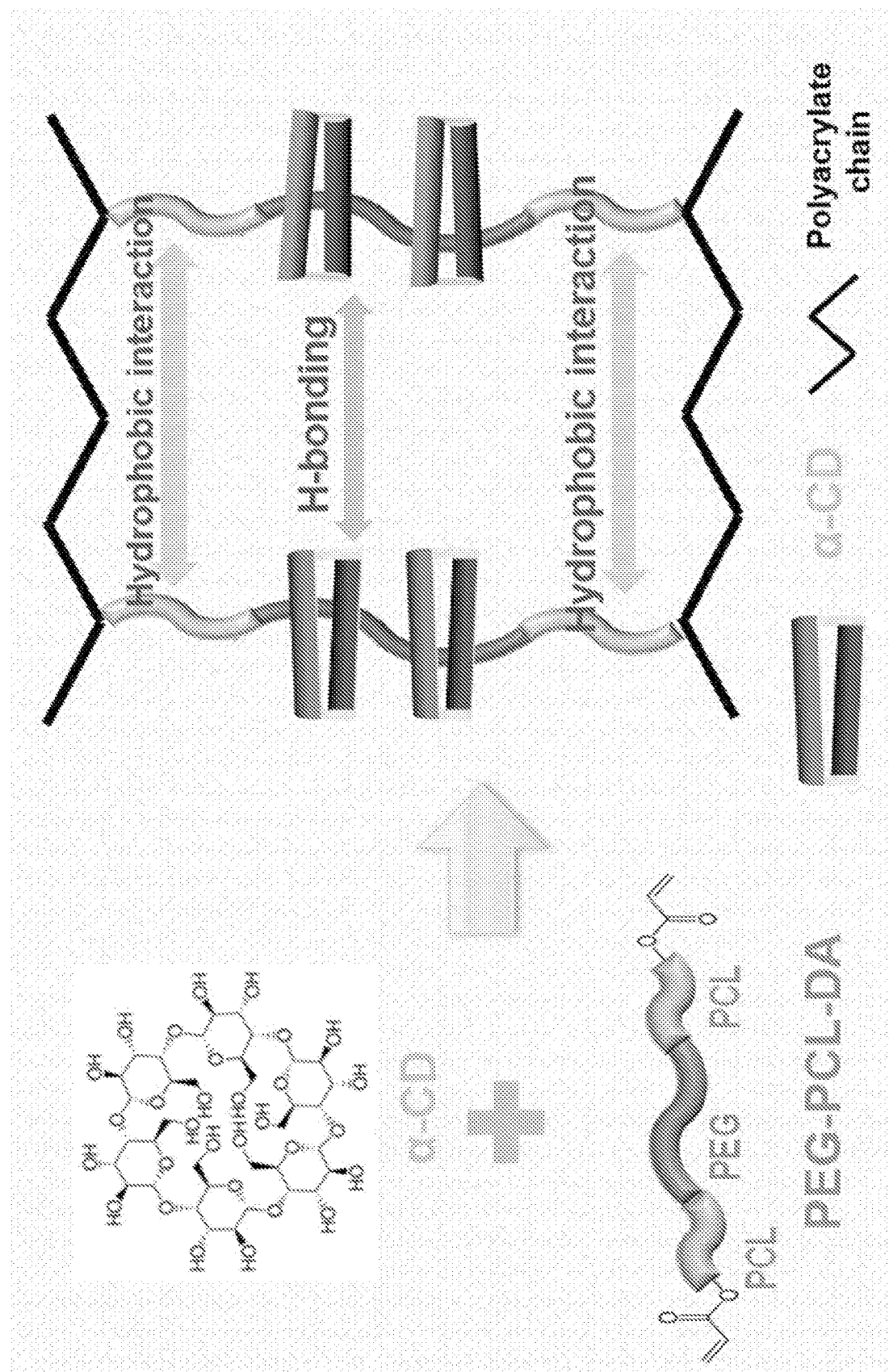
FIG. 10 shows how supermolecules can be combined to enhance printability.
Figure 11:
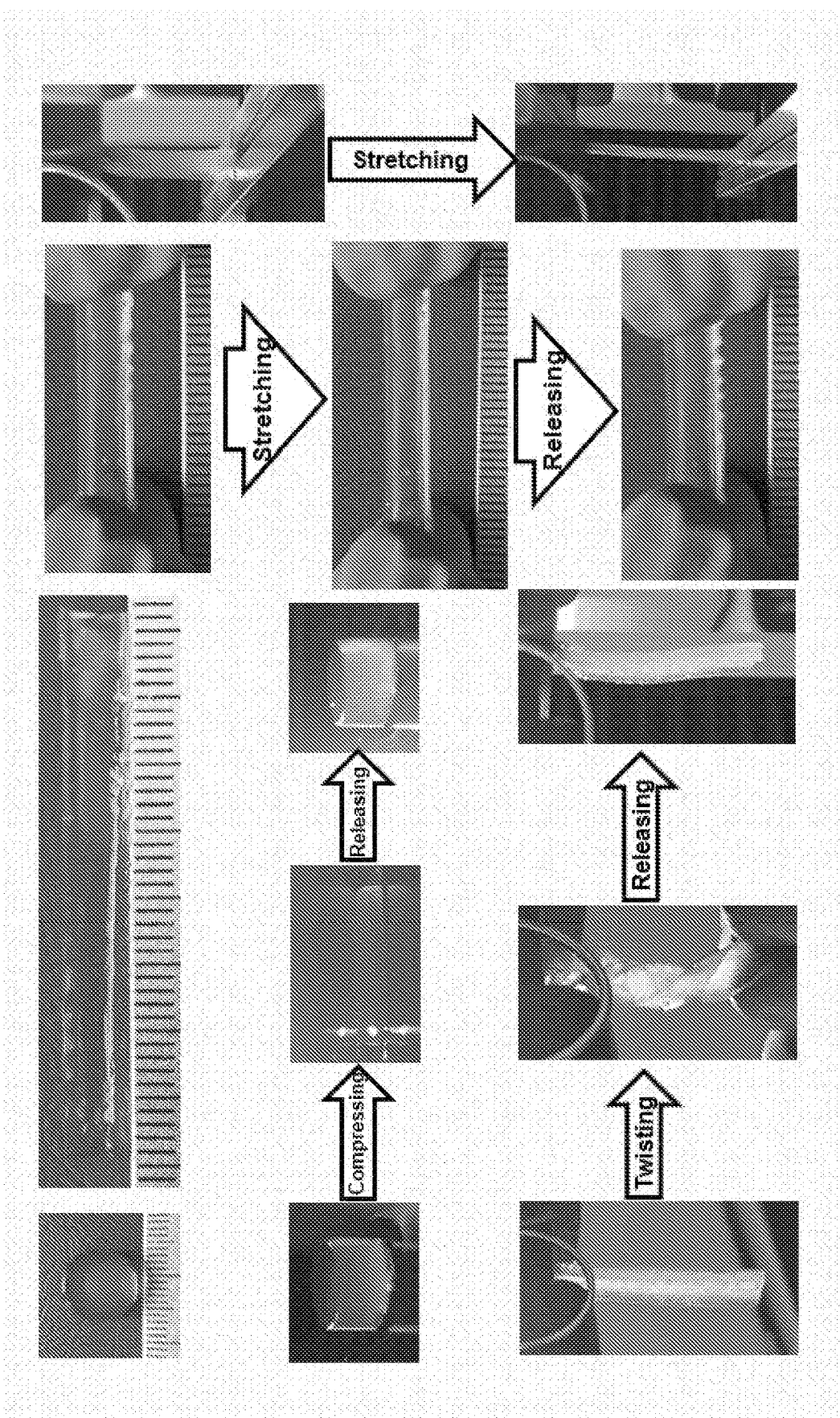
FIG. 11 shows macroscopic pictures which depict mechanical behaviors of PEG-PCL-DA/CD hydrogel.
Figures 12A, 12B:
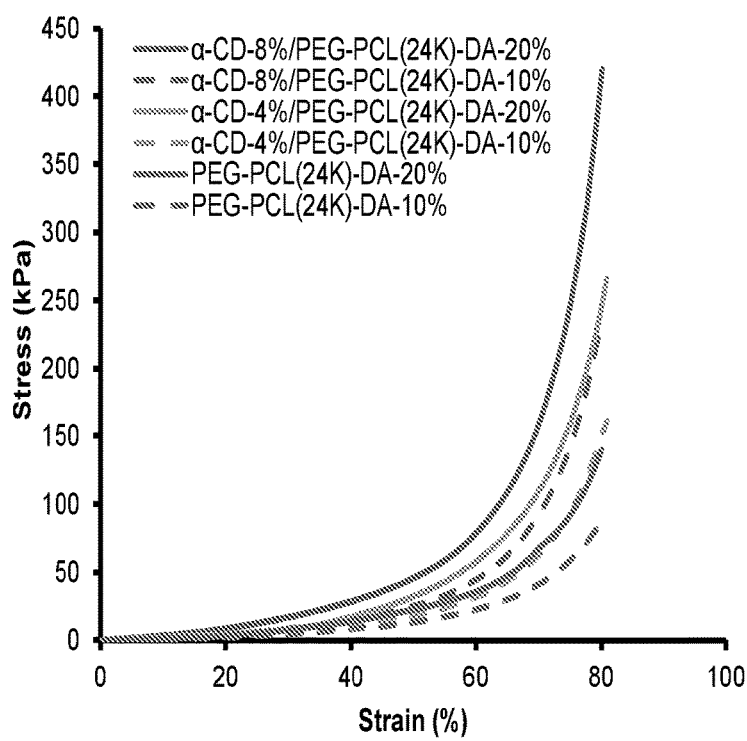
FIG. 12A-B shows compressive properties and water absorption.
Figures 13A, 13B:
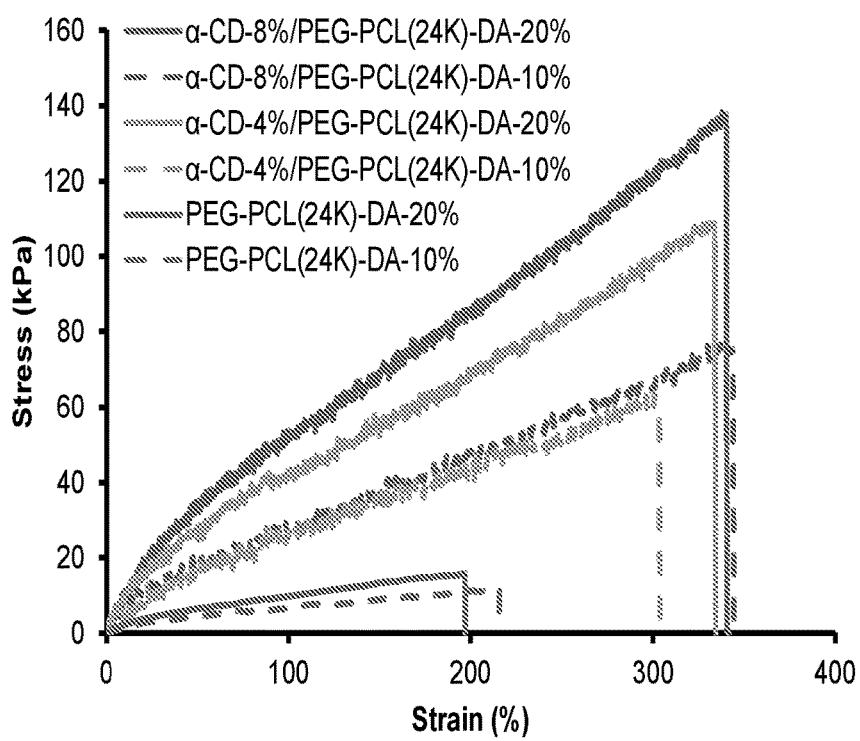
FIG. 13A-B shows tensile properties. 13A shows tensile properties & suture retention.
Figure 14A:
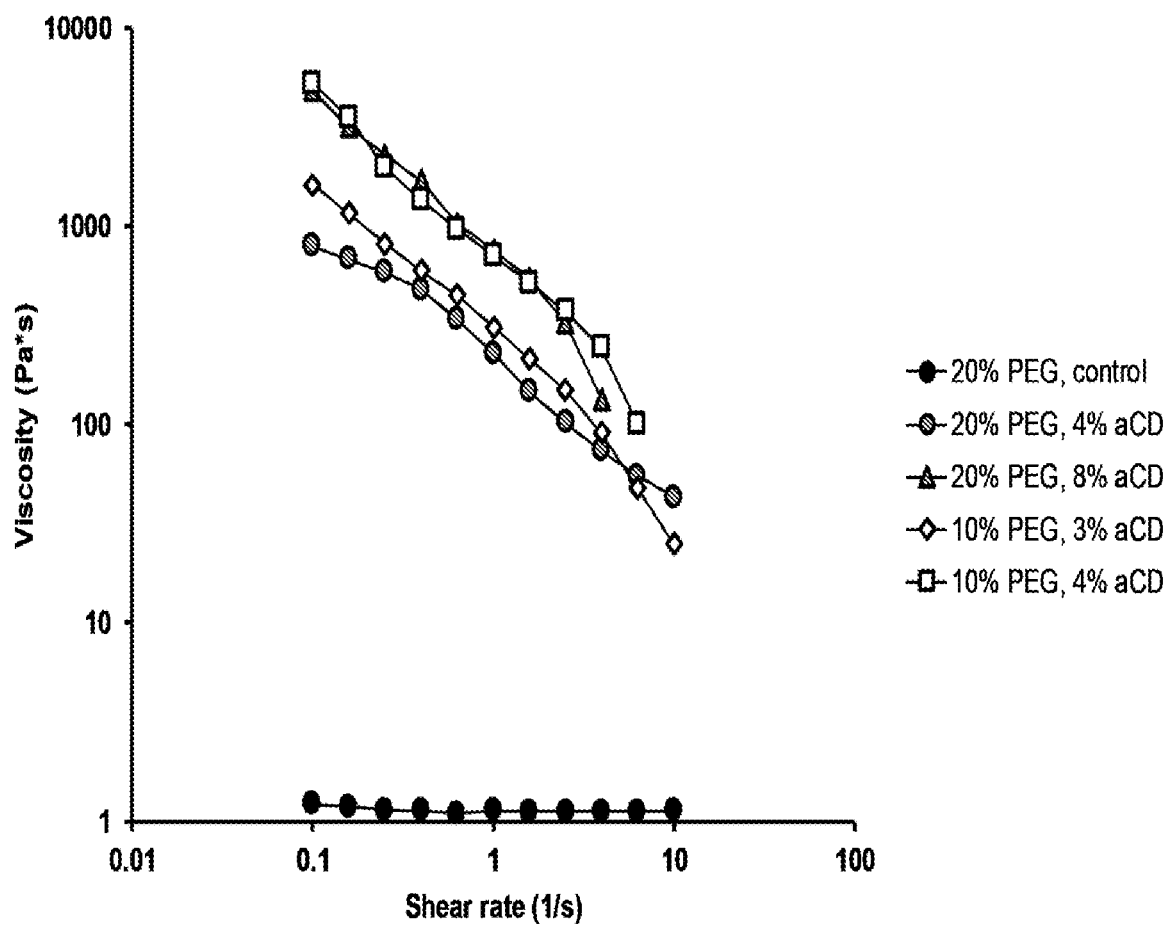
FIG. 14A-F shows rheological properties.
Figure 14B:
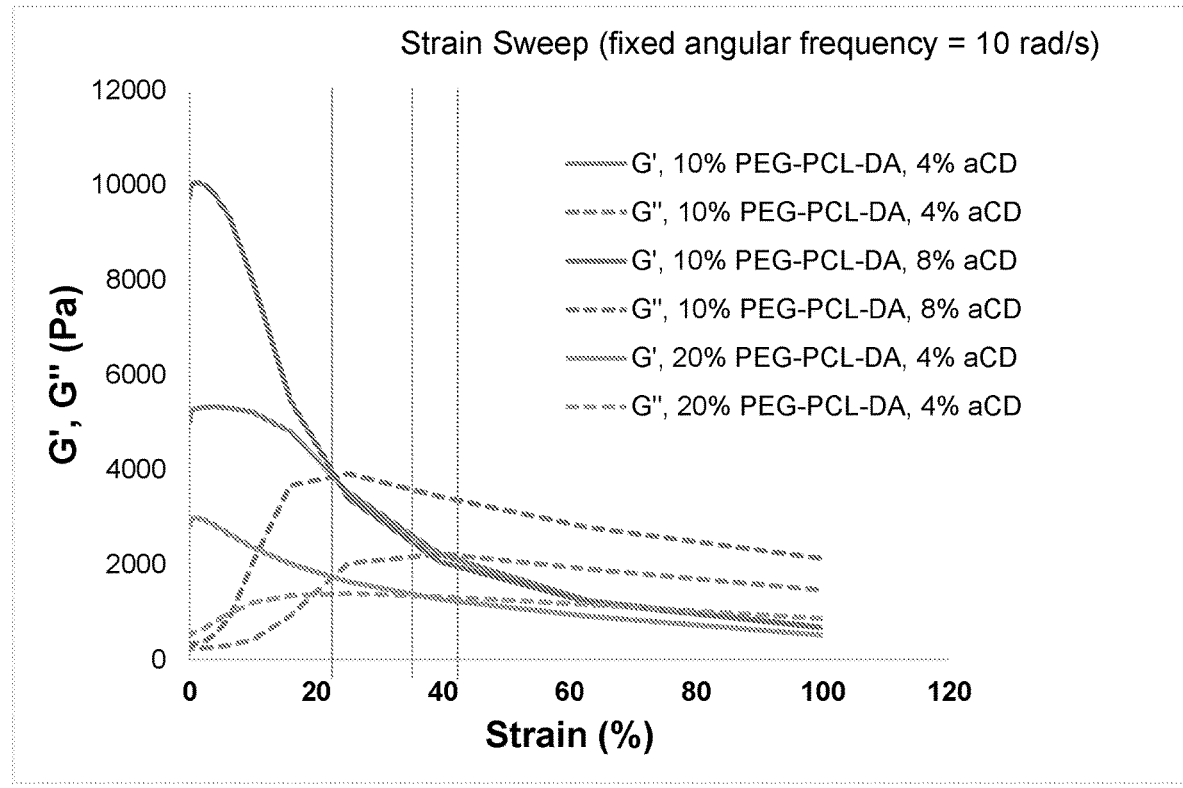
Figure 14C:
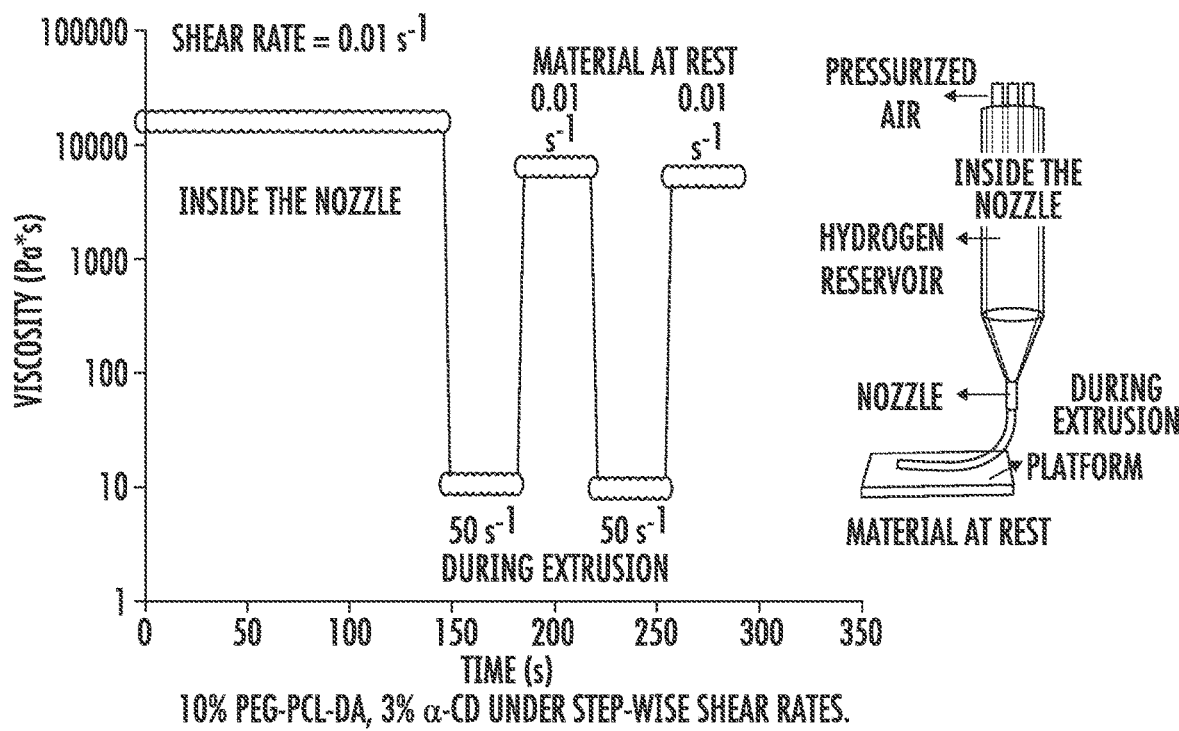
Figure 14D:
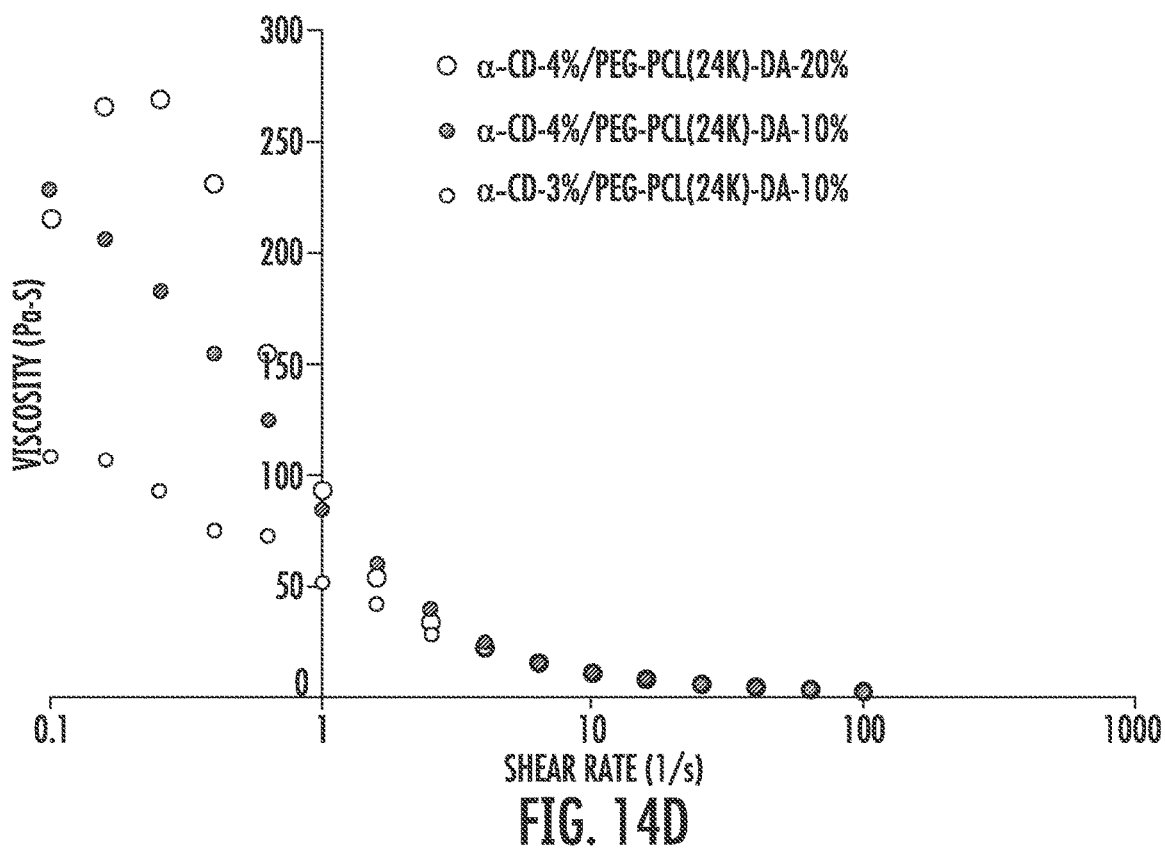
Figure 14E:
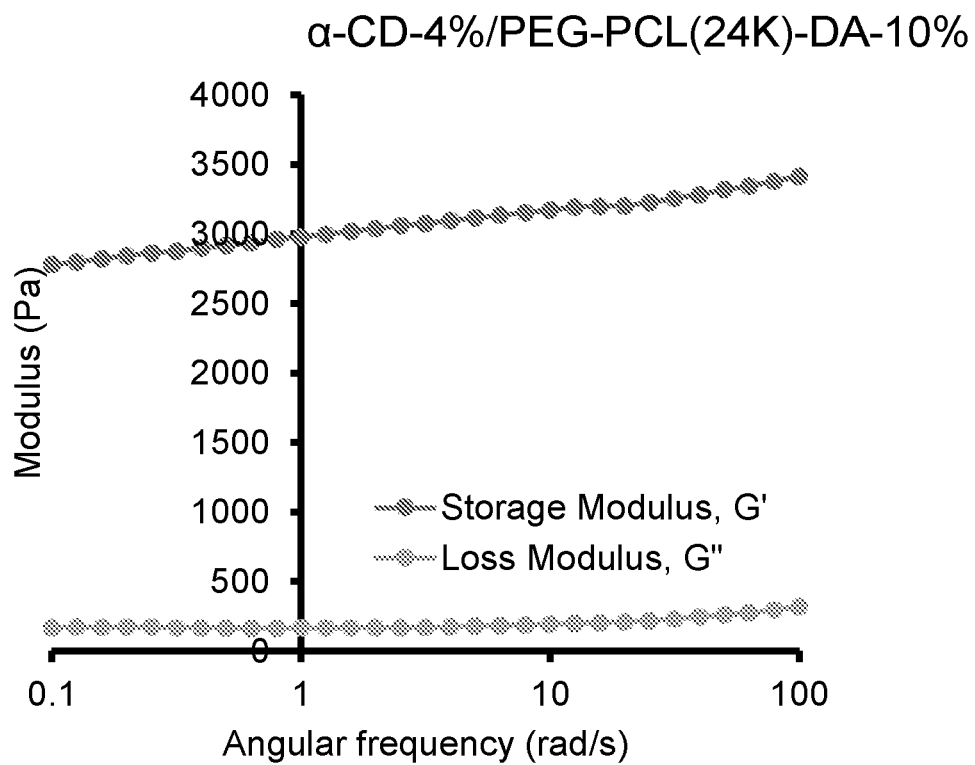
Figure 14F:
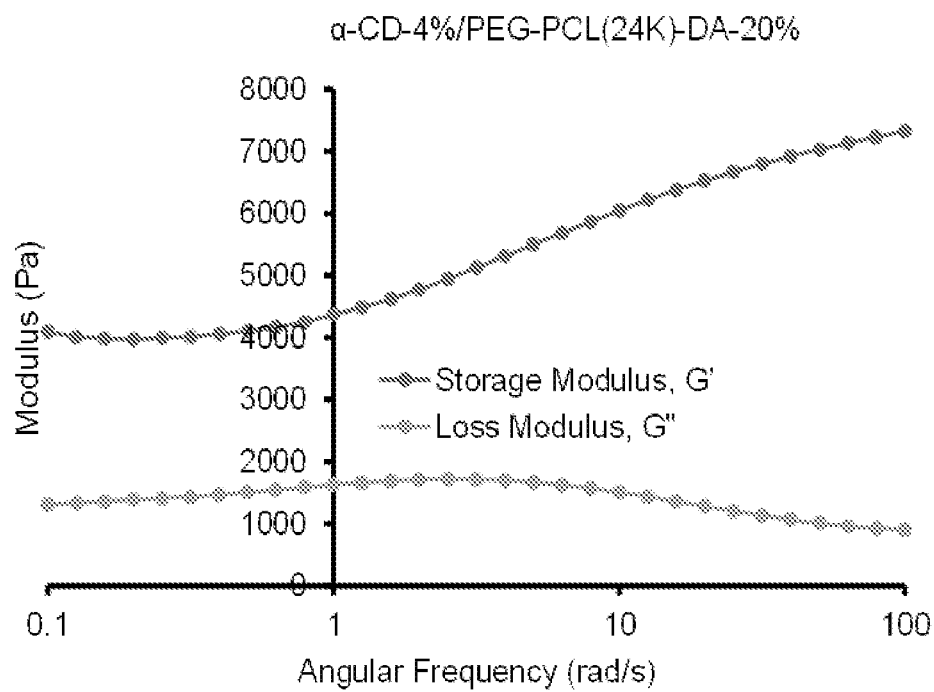
Figure 15A:
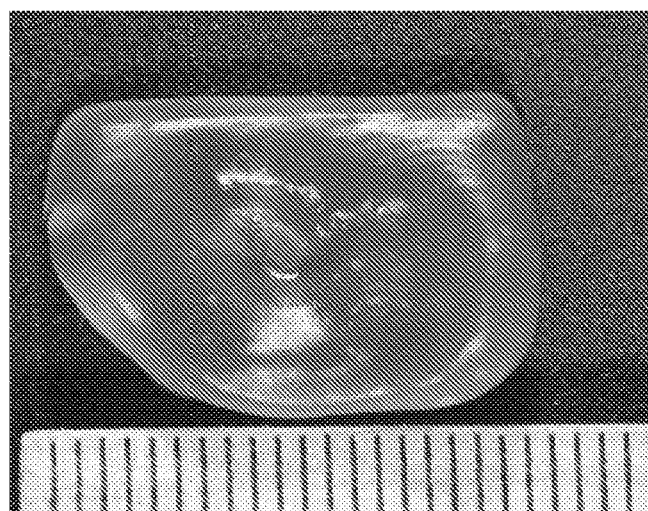
FIG. 15A-B shows an ear-shaped hydrogel printed with PEG-PCL-DA 10%/CD (2%).
Figure 15B:
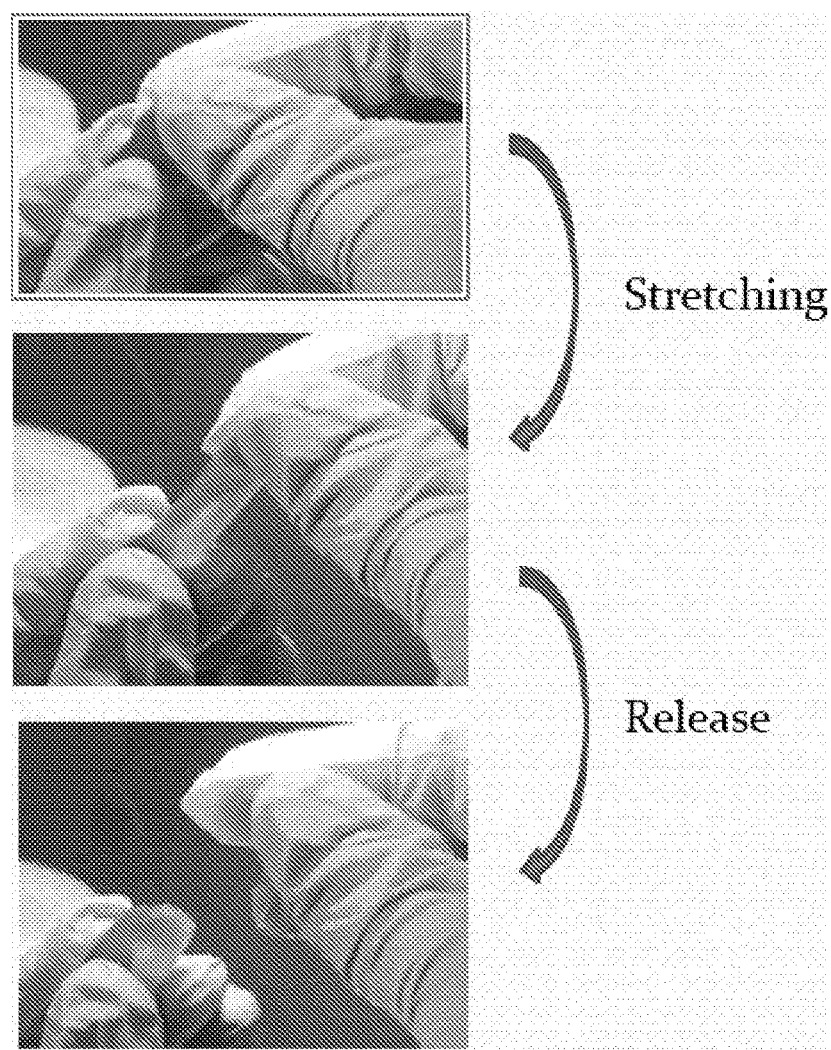

All hydrogels exhibited a large hysteresis loop in the first cycle, and much smaller hysteresis loops in the next nine cycles. Irreversible deformations decreased with increasing block length of PCL segments in the PEG-PCL-DA polymer chain from PEG-DA (~45%) to PEG-PCL(24K)-DA (~20%). As PCL amounts increased, PEG-PCL-DA hydrogel had increased capacity to hold its own weight when suspended from a cantilever after gelation. For instance, while PEG-DA maintained an angle of only 8° between the plane of the hydrogel and a vertical plane when suspended from a cantilever (FIG. 9A), PEG-PCL(22K)-DA (FIG. 9B) and PEG-PCL(24K)-DA (FIG. 9C) maintained angles of 20° and 39° under the same conditions, respectively.

Mechanical properties results showed that incorporation of PCL segments enhanced the strength, toughness, flexibility and elasticity of the single component hydrogel network. Without wishing to be bound by any one particular theory, these observations may primarily be attributed to hydrophobic interactions between PCL moieties in the hydrogel network. Hydrophobic interactions can form a second physical network in addition to a chemical crosslinking network, which can dissipate the crack energy applied along the hydrogel due to reversible dissociation of hydrophobic interactions.[47, 48]

The herein disclosed PEG-PCL-DA hydrogels thus have good mechanical strength and elasticity, and are useful for soft tissue engineering. For example, the initial moduli of PEG-PCL(24K)-DA-40% (37.7±1.7 kPa), PEG-PCL(22K)-DA-40% (28.2±2.4 kPa), PEG-PCL(24K)-DA-20% (16.4±4.8 kPa) and PEG-PCL(22K)-DA-20% (10.7±1.7 kPa) are within the range of that of human myocardium ($E_{myocardium}$=10-500 KPa).[49] The initial moduli of PEG-PCL(24K)-DA-20% (16.4±4.8 kPa), PEG-PCL(24K)-DA-10% (9.4±1.9 kPa) and PEG-PCL(22K)-DA-20% (10.7±1.7 kPa) are comparable to that of human muscle ($E_{muscle}$=8-17 kPa).[50]

Figure 5A:
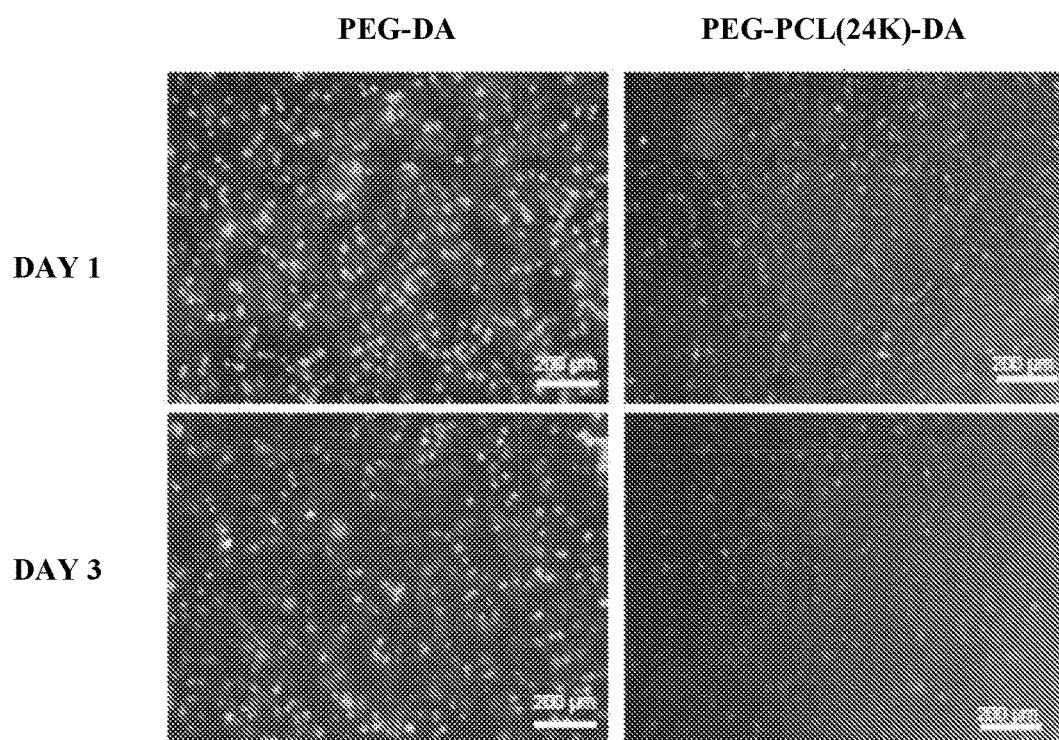
FIGS. 5A through 5C show in vitro cytocompatibility of elastic hydrogels.

In vitro cytocompatibility of PEG-PCL-DA hydrogel. The two polymer components in the hydrogel, PEG and PCL, are biocompatible materials used in FDA approved devices.[31] Hence, the hydrogel contains two moieties which likely possess good cytocompatibility. The ability of PEG-PCL-DA hydrogel to support encapsulated cell growth was evaluated using mouse 3T3 fibroblasts. Live/dead staining was used to determine cell viability in the hydrogel over 3 days of culture. 3T3 fibroblasts maintained a round morphology inside the PEG-DA hydrogel at day 1 and day 3 (FIG. 5A). However, a portion of 3T3 fibroblasts exhibited elongated cell morphology after one day of culture inside the PEG-PCL(24K)-DA hydrogel, showing the ability of PEG-PCL(24K)-DA hydrogel to support cell attachment. The hydrophobic PCL moiety facilitates protein adsorption to the hydrogel, thus, improving cell-hydrogel interactions.[33, 51]

Figure 5B:
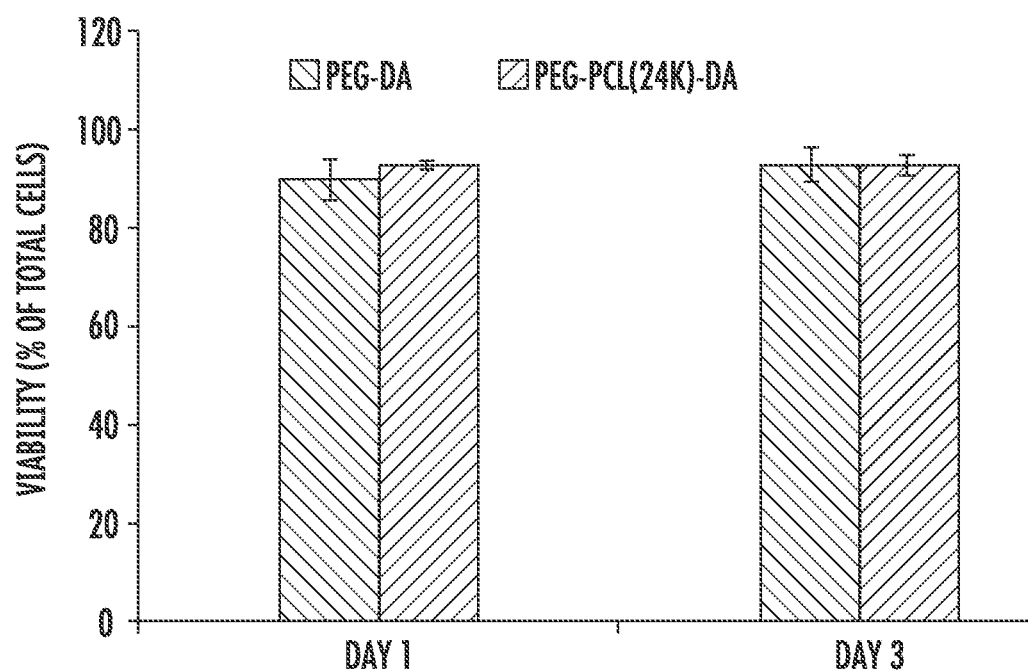
Figure 5C:
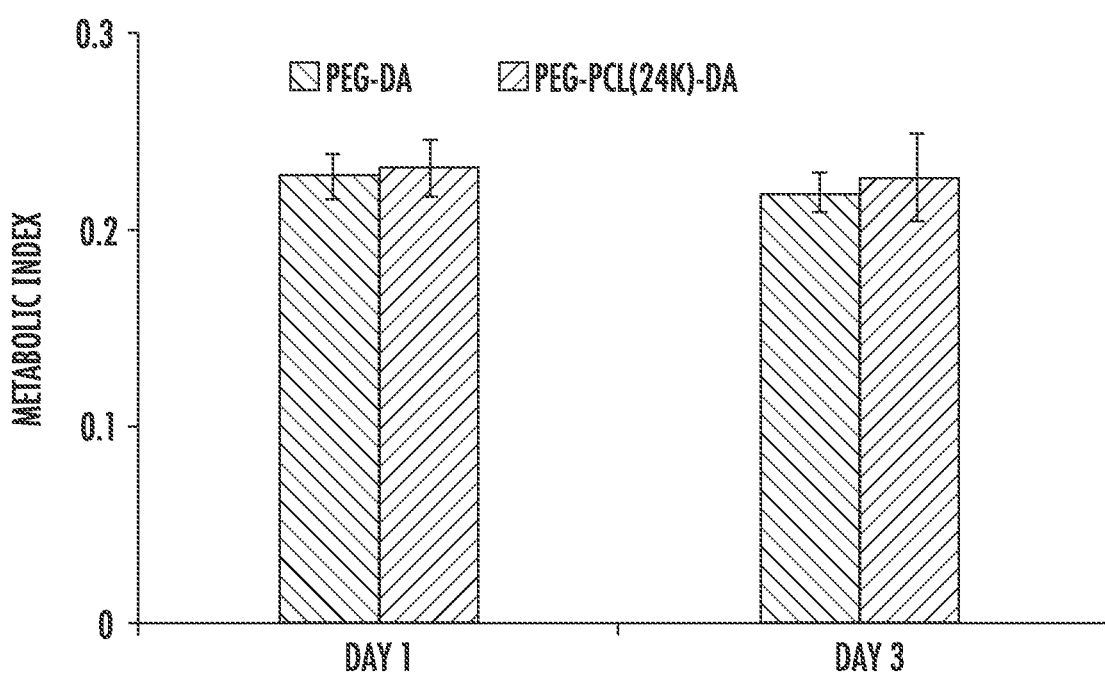

Cells encapsulated in PEG-based synthetic hydrogels are difficult to spread out because the high hydrophilicity of inert hydrogels resists protein adhesion and cannot support interactions between cells and hydrogels.[52] Incorporating bioactive components such as proteins, peptides and polysaccharides into the synthetic networks can significantly improve cell growth.[53-55] For example, cells with rounded morphology were observed in PEG hydrogels; however, cells exhibited spreading morphology inside the hydrogels after addition of hyaluronic acid or fibrinogen.[54, 55] Furthermore, 3T3 fibroblast survival rates inside the PEG-PCL(24K)-DA and PEG-DA hydrogels were over 90% from day 1 to day 3 (FIG. 5B). No significant difference in cell viability was observed between PEG-PCL(24K)-DA and PEG-DA hydrogels within 3 days of culture (p>0.05) (FIG. 5C). These results show PEG-PCL-DA hydrogel has good cell compatibility and supports growth of photo-encapsulated 3T3 fibroblasts in vitro.

Viscosity of PEG-PCL-DA Solution.

Figure 6A:
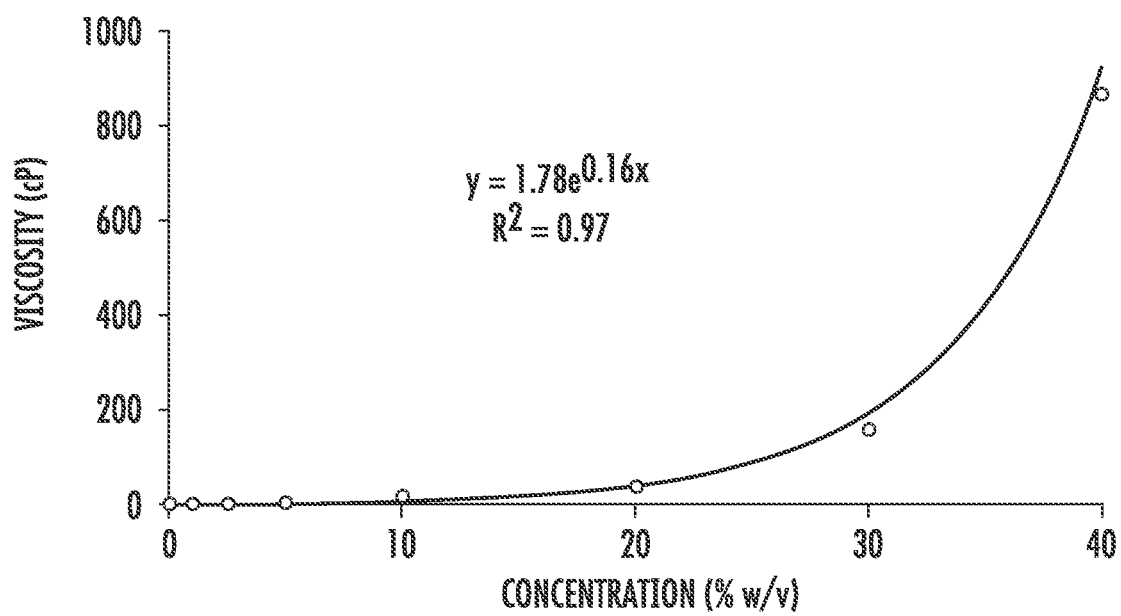
FIGS. 6A through 6G show cytotoxicity and printability of elastic PEG-PCL(24K)-DA hydrogel using an extrusion bioprinter.

Viscosity of the hydrogel precursors can be tuned for bioprinting. The viscosity of PEG-PCL-DA precursors increased exponentially with concentration (FIG. 6A). In particular, precursors in concentrations exceeding 30% (wt/v) showed remarkably increased viscosity with respect to their concentration, while 0-20% precursor solution had very low viscosity. Different bioprinting techniques may be needed for hydrogels at different viscosities. For example, an inkjet-based printer can be used for a precursor solution below 20% concentration. For higher concentration solutions, an extrusion-based printer suitable for printing high viscous materials can be used.

Cellular Printing.

Figure 6B:
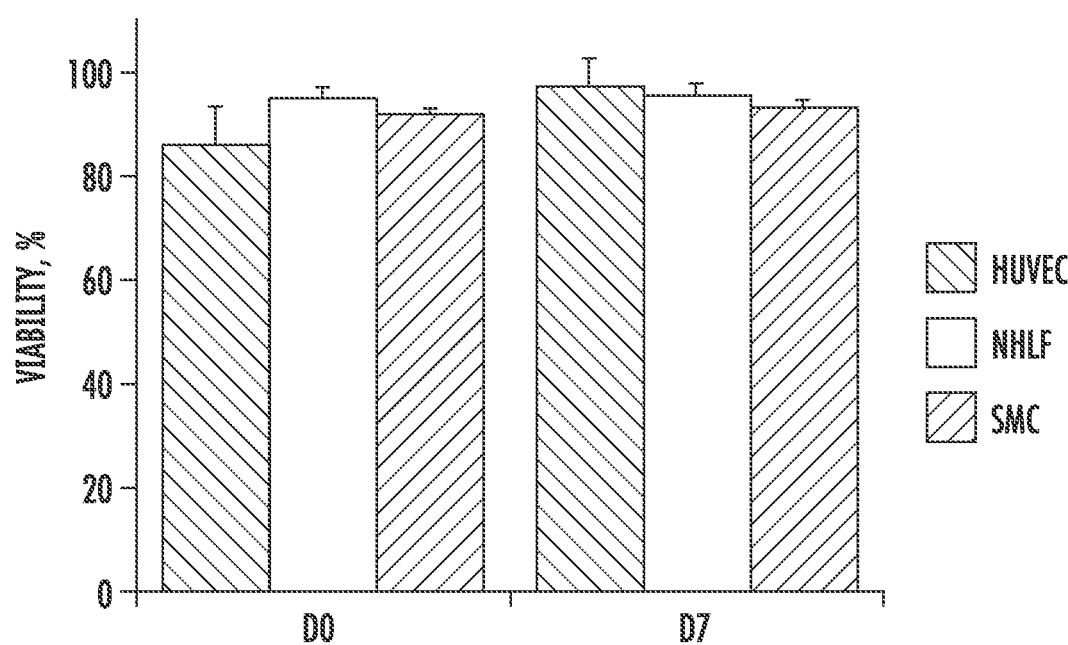
Figure 6C:
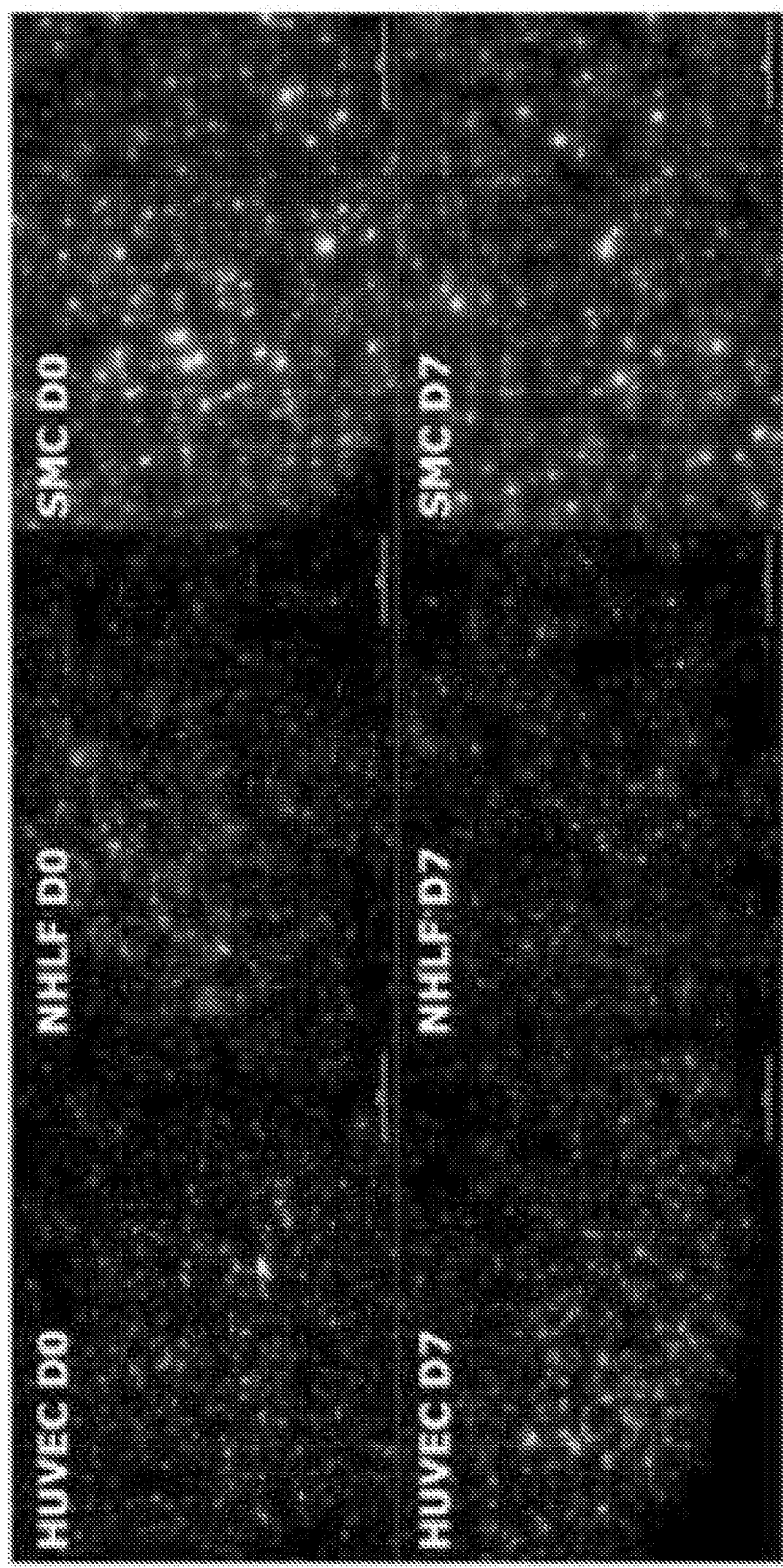
Figure 6D:
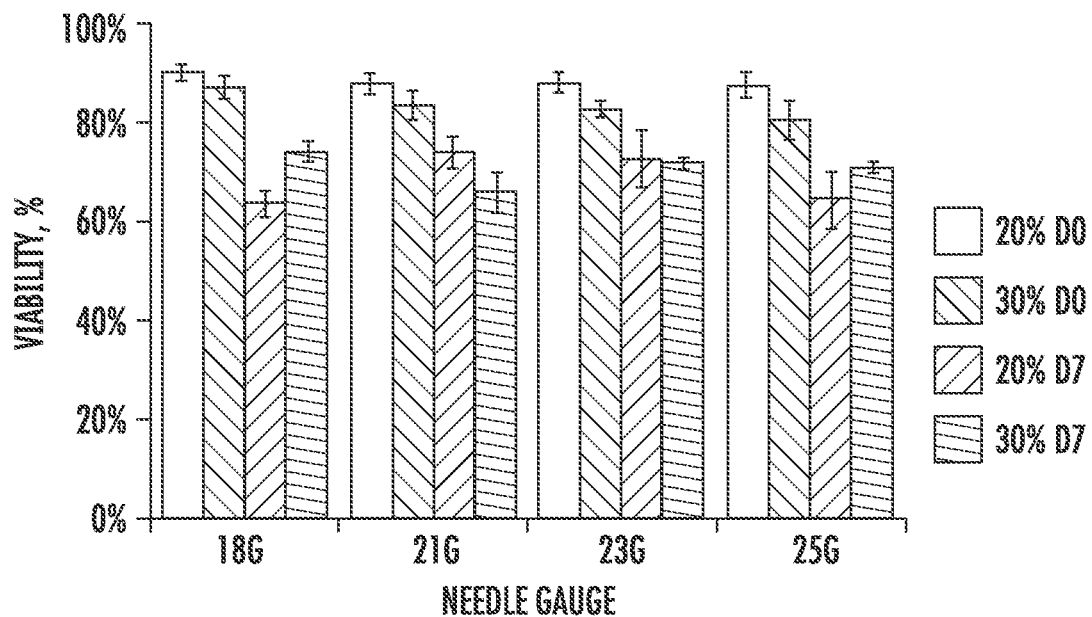
Figure 6E:
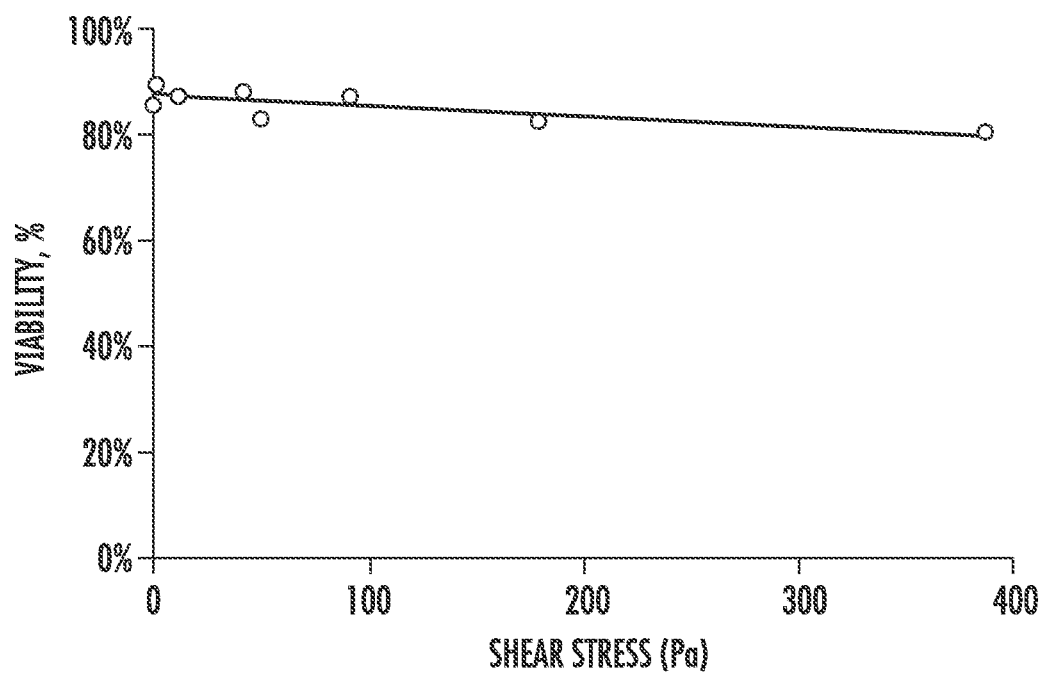

Hydrogel loaded with the cells was printed to test whether the material can be applied in bioprinting cell-gel constructs. For constructs printed with PEG-PCL(24K)-DA at 10% of polymer concentration, a cell viability of over 83% was observed across three different human cell types: human umbilical vein endothelial cells, neonatal human lung fibroblasts, and human aortic smooth muscle cells. These results demonstrate PEG-PCL-DA can be used to print material modeling a wide range of different human soft tissues. The cells within the constructs continued to exhibit high viability after 7 days in culture printing (FIGS. 6B and 6C). No significant difference in cell viability was observed with decreasing nozzle diameter immediately after printing (FIG. 6D). Similarly, no significant difference in cell viability with increasing shear stress was observed (FIG. 6E). However, a significant decrease in cell viability occurred after 7 days in culture (FIG. 6D). This could be a result of decreased nutrient diffusion from polymer having increased concentration and/or cell damage experienced from the printing process.

Figure 6F:
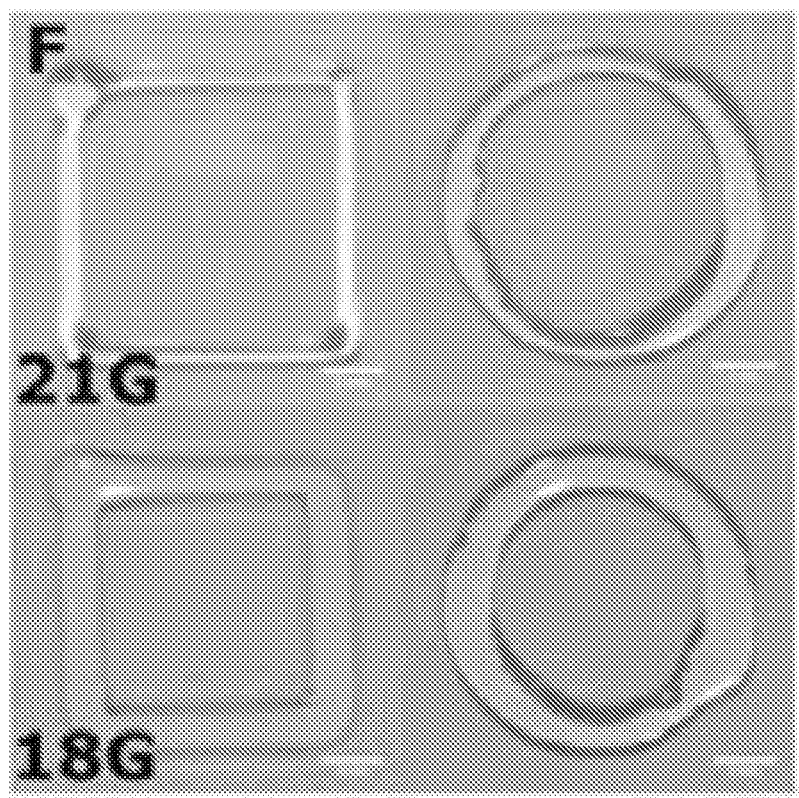
Figure 6G:
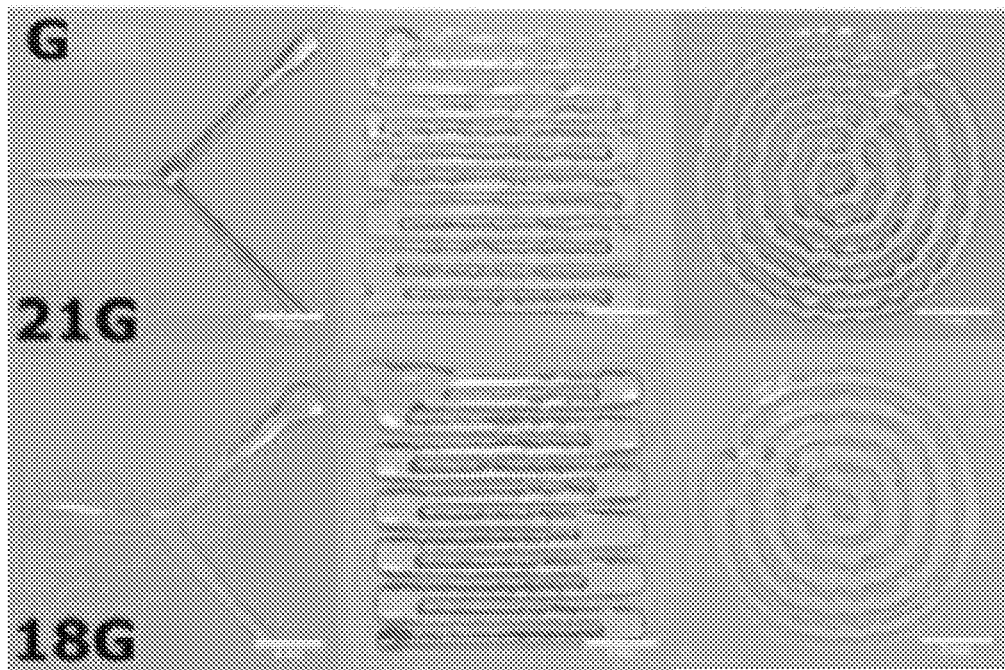

PEG-PCL-DA hydrogels also can be easily printed in various patterns. Basic geometric shapes were printed using PEG-PCL-DA precursor, and resolution was adjustable by changing nozzle diameter (FIG. 6F). Complex patterns could also be achieved by modifying the printing pattern on the cell printing platform. However, the polymer solution spread as it contacted the substrate, limiting the minimum feature size (FIG. 6G).

In summary, disclosed herein is a visible light crosslinked, single-component, elastic and biodegradable hydrogel system based on a triblock copolymer of PEG and PCL. The system is biocompatible, biodegradable and has tunable mechanical properties. The desirable elastic properties are conducive for soft tissue engineering because an elastic material capable of transducing correct mechanical stimulation to cells can improve tissue adaptation to biomechanical environment. Various cells can be incorporated with the hydrogel for bioprinting. The polymeric components are FDA approved, facilitating use in preclinical and clinical trials. The disclosed hydrogels are compatible with many other biomaterial approaches, such as incorporation of biomimetic peptides, proteins, growth factors or other bioactive molecules.

Example 2: Shear-Thinning Biodegradable Hydrogel with High Elasticity for 3D Bioprinting Three-dimensional (3D) bioprinting have been widely used in tissue engineering to replace or regenerate defective tissues, in which cells and biomaterials are used as "bioink" and deposited simultaneously (Soroosh D, et al. Bioact Mater. 2018; 3: 144-156.) Hydrogels have been considered as attractive materials for bioink because of their high-water content and low toxicity giving them good mimics of extracellular matrix (Tibbitt M W, et al. Biotechnol Bioeng. 2009; 103: 655-63). There are two main challenges for 3D bioprinting hydrogels, one is achieving shape fidelity while printing, and the other is providing enough mechanical properties to mimic native resilient soft tissues. A visible light crosslinked, single-network, biodegradable hydrogel, poly(ethylene glycol-co-caprolactone) diacrylate (PEG-PCL-DA), with high elasticity and flexibility for cell printing was previously synthesized (Xu C, et al. ACS Appl. Mater. Interfaces. 2018; 10:9969-79). However, when α-cyclodextrin (α-CD) with good biocompatibility is introduced into the PEG-PCL-DA photo-crosslinked network, in which an inclusion complex is formed between the PEG-PCL-DA and α-CD by hydrophobic interactions, and then stabilized by the hydrogen bonding between the neighboring α-CDs, good results are obtained. (Li J, et al. J Biomed Mater Res A. 2003; 65:196-202). The introduction of α-CD can therefore enhance the mechanical properties of PEG-PCL-DA hydrogel, and improve its viscosity and shear-thinning property.

The introduction of α-CD into the PEG-PCL-DA hydrogel network can greatly strengthen the mechanical properties of the PEG-PCL-DA hydrogel and showed good shear-thinning properties. This study demonstrates the use of cyclodextrins to enhance hydrogel mechanical and shear thinning properties for 3D bioprinting application.

REFERENCES (1) Murphy, S. V.; Atala, A. 3D Bioprinting of Tissues and Organs. *Nature biotechnol.* 2014, 32, 773-785.

(2) Lin, K. F.; He, S.; Song, Y.; Wang, C. M.; Gao, Y.; Li, J. Q.; Tang, P.; Wang, Z.; Bi, L.; Pei, G. X. Low-Temperature Additive Manufacturing of Biomimic Three-Dimensional Hydroxyapatite/Collagen Scaffolds for Bone Regeneration. *ACS Appl. Mater. Interfaces.* 2016, 8, 6905-6916.

(3) Yu, Y.; Hua, S.; Yang, M.; Fu, Z.; Teng, S.; Niu, K.; Zhao, Q.; Yi, C. Fabrication and Characterization of electrospinning/3D Printing Bone Tissue Engineering Scaffold. *RSC Adv.* 2016, 6, 110557-110565.

(4) Lee, S. J.; Lee, D.; Yoon, T. R.; Kim, H. K.; Jo, H. H.; Park, J. S.; Lee, J. H.; Kim, W. D.; Kwon, I. K.; Park, S. A. Surface Modification of 3D-Printed Porous Scaffolds via Mussel-Inspired Polydopamine and Effective Immobilization of rhBMP-2 to Promote Osteogenic Differentiation for Bone Tissue Engineering. *Acta Biomater.* 2016, 40, 182-191.

(5) Inzana, J. A.; Olvera, D.; Fuller, S. M.; Kelly, J. P.; Graeve, O. A.; Schwarz, E. M.; Kates, S. L.; Awad, H. A. 3D Printing of Composite Calcium Phosphate and Collagen Scaffolds for Bone Regeneration. *Biomaterials* 2014, 35, 4026-4034.

(6) Cui, X.; Boland, T. Human Microvasculature Fabrication Using Thermal Inkjet Printing Technology. *Biomaterials* 2009, 30, 6221-6227.

(7) Wang, X.; Yan, Y.; Pan, Y.; Xiong, Z.; Liu, H.; Cheng, J.; Liu, F.; Lin, F.; Wu, R.; Zhang, R.; Lu, Q. Generation of Three-Dimensional Hepatocyte/Gelatin Structures with Rapid Prototyping System. *Tissue Eng.* 2006, 12, 83-90.

(8) Lee, V.; Singh, G.; Trasatti, J. P.; Bjornsson, C.; Xu, X.; Tran, T. N.; Yoo, S.-S.; Dai, G.; Karande, P. Design and Fabrication of Human Skin by Three-Dimensional Bioprinting. *Tissue Eng Part C: Methods* 2014, 20, 473-484.

(9) Xu, T.; Gregory, C. A.; Molnar, P.; Cui, X.; Jalota, S.; Bhaduri, S. B.; Boland, T. Viability and Electrophysiology of Neural Cell Structures Generated by the Inkjet Printing Method. *Biomaterials* 2006, 27, 3580-3588.

(10) Xu, C.; Chai, W.; Huang, Y.; Markwald, R. R. Scaffold-Free Inkjet Printing of Three-Dimensional Zigzag Cellular Tubes. *Biotechnol Bioeng* 2012, 109, 3152-3160.

(11) Fedorovich, N. E.; De Wijn, J. R.; Verbout, A. J.; Alblas, J.; Dhert, W. J. Three-Dimensional Fiber Deposition of Cell-Laden, Viable, Patterned Constructs for Bone Tissue Printing. *Tissue Eng Part A* 2008, 14, 127-133.

(12) Hoffman, A. S. Hydrogels for Biomedical Applications. *Adv. Drug Deliv. Rev.* 2012, 64, 18-23.

(13) Arcaute, K.; Mann, B. K.; Wicker, R. B. Stereolithography of Three-Dimensional Bioactive Poly(ethylene glycol) Constructs with Encapsulated Cells. *Ann. Biomed. Eng.* 2006, 34, 1429-1441.

(14) Billiet, T.; Gevaert, E.; De Schryver, T.; Cornelissen, M.; Dubruel, P. The 3D Printing of Gelatin Methacrylamide Cell-Laden Tissue-Engineered Constructs with High Cell Viability. *Biomaterials* 2014, 35, 49-62.

(15) Bertassoni, L. E.; Cardoso, J. C.; Manoharan, V.; Cristino, A. L.; Bhise, N. S.; Araujo, W. A.; Zorlutuna, P.; Vrana, N. E.; Ghaemmaghami, A. M.; Dokmeci, M. R.;

Khademhosseini, A. Direct-Write Bioprinting of Cell-Laden Methacrylated Gelatin Hydrogels. *Biofabrication* 2014, 6, 024105.

(16) Knowlton, S.; Yu, C. H.; Ersoy, F.; Emadi, S.; Khademhosseini, A.; Tasoglu, S. 3D-Printed Microfluidic Chips with Patterned, Cell-Laden Hydrogel Constructs. *Biofabrication* 2016, 8, 025019.

(17) Zhang, K.; Fu, Q.; Yoo, J.; Chen, X.; Chandra, P.; Mo, X.; Song, L.; Atala, A.; Zhao, W. 3D Bioprinting of Urethra with PCL/PLCL Blend and Dual Autologous Cells in Fibrin Hydrogel: an in vitro Evaluation of Biomimetic Mechanical Property and Cell Growth environment. *Acta Biomater.* 2017, 50, 154-164.

(18) Gao, G.; Schilling, A. F.; Hubbell, K.; Yonezawa, T.; Truong, D.; Hong, Y.; Dai, G.; Cui, X. Improved Properties of Bone and Cartilage Tissue from 3D Inkjet-Bioprinted Human Mesenchymal Stem Cells by Simultaneous Deposition and Photocrosslinking in PEG-GelMA. *Biotechnol lett.* 2015, 37, 2349-2355.

(19) Xu, T.; Binder, K. W.; Albanna, M. Z.; Dice, D.; Zhao, W.; Yoo, J. J.; Atala, A. Hybrid Printing of Mechanically and Biologically Improved Constructs for Cartilage Tissue Engineering Applications. *Biofabrication* 2013, 5, 015001.

(20) Hong, S.; Sycks, D.; Chan, H. F.; Lin, S.; Lopez, G. P.; Guilak, F.; Leong, K. W.; Zhao, X. 3D Printing of Highly Stretchable and Tough Hydrogels into Complex, Cellularized Structures. *Adv. Mater.* 2015, 27, 4035-4040.

(21) Yang, F.; Tadepalli, V.; Wiley, B. J. 3D Printing of A Double Network Hydrogel with A Compression Strength and Elastic Modulus Greater than those of Cartilage. *ACS Biomater. Sci. Eng.* 2017, 3, 863-869.

(22) Wei, J.; Wang, J.; Su, S.; Wang, S.; Qiu, J.; Zhang, Z.; Christopher, G.; Ning, F.; Cong, W. 3D Printing of An Extremely Tough Hydrogel. *RSC Adv.* 2015, 5, 81324-81329.

(23) Guilak, F.; Butler, D. L.; Goldstein, S. A.; Baaijens, F. P. Biomechanics and Mechanobiology in Functional Tissue Engineering. *J. Biomech.* 2014, 47, 1933-1940.

(24) Xu, C.; Huang, Y.; Tang, L.; Hong, Y. Low-Initial-Modulus Biodegradable Polyurethane Elastomers for Soft Tissue Regeneration. *ACS Appl. Mater. Interfaces* 2017, 9, 2169-2180.

(25) Hem, D. L.; Hubbell, J. A. Incorporation of Adhesion Peptides into Nonadhesive Hydrogels Useful for Tissue Resurfacing. *J. Biomed. Mater. Res.* 1998, 39, 266-276.

(26) Fairbanks, B. D.; Schwartz, M. P.; Bowman, C. N.; Anseth, K. S. Photoinitiated Polymerization of PEG-Diacrylate with Lithium Phenyl-2,4,6-Trimethylbenzoylphosphinate: Polymerization Rate and Cytocompatibility. *Biomaterials* 2009, 30, 6702-6707.

(27) Majima, T.; Schnabel, W.; Weber, W. Phenyl-2,4,6-Trimethylbenzoylphosphinates as Water-Soluble Photoinitiators. Generation and Reactivity of $O=\dot{P}(C_6H_5)(O^-)$ Radical Anions. *Macromol Chem Phys.* 1991, 192, 2307-2315.

(28) Park, H.; Guo, X.; Temenoff, J. S.; Tabata, Y.; Caplan, A. I.; Kasper, F. K.; Mikos, A. G. Effect of Swelling Ratio of Injectable Hydrogel Composites on Chondrogenic Differentiation of Encapsulated Rabbit Marrow Mesenchymal Stem Cells in vitro. *Biomacromolecules*, 2009, 10, 541-546.

(29) Wu, J.; Ding, Q.; Dutta, A.; Wang, Y.; Huang, Y. H.; Weng, H.; Tang, L.; Hong, Y. An Injectable Extracellular Matrix Derived Hydrogel for Meniscus Repair and Regeneration. *Acta Biomater.* 2015, 16, 49-59.

(30) Chuang, T. W.; Masters, K. S. Regulation of Polyurethane Hemocompatibility and Endothelialization by Tethered Hyaluronic Acid Oligosaccharides. *Biomaterials* 2009, 30, 5341-5351.

(31) Xu, C.; Huang, Y.; Wu, J.; Tang, L.; Hong, Y. Triggerable Degradation of Polyurethanes for Tissue Engineering Applications. *ACS Appl Mater Interface* 2015, 7, 20377-20388.

(32) Xu, C.; Huang, Y.; Yepez, G.; Wei, Z.; Liu, F.; Bugarin, A.; Tang, L.; Hong, Y. Development of Dopant-Free Conductive Bioelastomers. *Sci Rep.* 2016, 6, 34451.

(33) Zhang, C.; Aung, A.; Liao, L.; Varghese, S. A Novel Single Precursor-Based Biodegradable Hydrogel with Enhanced Mechanical Properties. *Soft Matter* 2009, 5, 3831-3834.

(34) Gong, C.; Shi, S.; Dong, P.; Kan, B.; Gou, M.; Wang, X.; Li, X.; Luo, F.; Zhao, X.; Wei, Y.; Qian, Z. Synthesis and Characterization of PEG-PCL-PEG Thermosensitive Hydrogel. *Int J Pharm.* 2009, 365, 89-99.

(35) Ma, G.; Miao, B.; Song, C. Thermosensitive PCL-PEG-PCL Hydrogels: Synthesis, Characterization, and Delivery of Proteins. *J. Appl. Polym. Sci.* 2010, 116, 1985-1993.

(36) Gong, C. Y.; Dong, P. W.; Shi, S.; Fu, S. Z.; Yang, J. L.; Guo, G.; Zhao, X.; Wei, Y. Q.; Qian, Z. Y. Thermosensitive PEG-PCL-PEG Hydrogel Controlled Drug Delivery System: Sol-Gel-Sol Transition and in vitro Drug Release Study *J Pharm Sci.* 2009, 98, 3707-3717.

(37) Mariner, P. D.; Wudel, J. M.; Miller, D. E.; Genova, E. E.; Streubel, S. O.; Anseth, K. S. Synthetic Hydrogel Scaffold is an Effective Vehicle for Delivery of INFUSE (rhBMP2) to Critical-Sized Calvaria Bone Defects in Rats. *J Orthop Res.* 2013, 31, 401-406.

(38) Burdick, J. A.; Chung, C.; Jia, X.; Randolph, M. A.; Langer, R. Controlled Degradation and Mechanical Behavior of Photopolymerized Hyaluronic Acid Networks. *Biomacromolecules* 2005, 6, 386-391.

(39) Schuurman, W.; Levett, P. A.; Pot, M. W.; van Weeren, P. R.; Dhert, W. J.; Hutmacher, D. W.; Melchels, F. P.; Klein, T. J.; Malda, J. Gelatin-Methacrylamide Hydrogels as Potential Biomaterials for Fabrication of Tissue-Engineered Cartilage Constructs. *Macromol Biosci.* 2013, 13, 551-561.

(40) Lim, K. S.; Schon, B. S.; Mekhileri, N. V.; Brown, G. C.; Chia, C. M.; Prabakar, S.; Hooper, G. J.; Woodfield, T. B. New Visible-Light Photoinitiating System for Improved Print Fidelity in Gelatin-Based Bioinks. *ACS Biomater. Sci. Eng.* 2016, 2, 1752-1762.

(41) Suntornnond, R.; Tan, E. Y. S.; An, J.; Chua, C. K. 2017. A Highly Printable and Biocompatible Hydrogel Composite for Direct Printing of Soft and Perfusable Vasculature-like Structures. *Sci Rep.* 2017, 7, 16902.

(42) Bakarich, S; E.; Gorkin III, R.; in het Panhuis, M.; Spinks, G. M. Three-Dimensional Printing Fiber Reinforced Hydrogel Composites. *ACS Appl Mater Interfaces.* 2014, 6, 15998-16006.

(43) Hölzl, K.; Lin, S.; Tytgat, L.; Van Vlierberghe, S.; Gu, L.; Ovsianikov, A. Bioink Properties Before, During and After 3D Bioprinting. *Biofabrication* 2016, 8, 032002.

(44) Malda, J.; Visser, J.; Melchels, F. P.; JUngst, T.; Hennink, W. E.; Dhert, W. J. A.; Groll, J.; Hutmacher, D. W. 25th Anniversary Article: Engineering Hydrogels for Biofabrication. *Adv. Mater.* 2013, 25, 5011-5028.

(45) Bukhari, S. M. H.; Khan, S.; Rehanullah, M.; Ranjha, N. M. 2015. Synthesis and Characterization of Chemically Cross-Linked Acrylic Acid/Gelatin Hydrogels:

Effect of pH and Composition on Swelling and Drug Release. *Int. J. Polym. Sci.* 2015, 2015, 1-15.

(46) Son, K. H.; Lee, J. W. Synthesis and Characterization of Poly (Ethylene Glycol) Based Thermo-Responsive Hydrogels for Cell Sheet Engineering. *Materials* 2016, 9, 854.

(47) Tuncaboylu, D. C.; Sari, M.; Oppermann, W.; Okay, O. Tough and Self-Healing Hydrogels Formed via Hydrophobic Interactions. *Macromolecules* 2011, 44, 4997-5005.

(48) Abdurrahmanoglu, S.; Can, V.; Okay, O. Design of High-Toughness Polyacrylamide Hydrogels by Hydrophobic Modification. *Polymer* 2009, 50, 5449-5455.

(49) Venugopal, J. R.; Prabhakaran, M. P.; Mukherjee, S.; Ravichandran, R.; Dan, K.; Ramakrishna, S. Biomaterial Strategies for Alleviation of Myocardial Infarction. *J. R. Soc. Interface* 2012, 9, 1-19.

(50) Engler, A. J.; Sen, S.; Sweeney, H. L.; Discher, D. E. Matrix Elasticity Directs Stem Cell Lineage Specification. *Cell* 2006, 126, 677-689.

(51) Schiraldi, C.; D'Agostino, A.; Oliva, A.; Flamma, F.; De Rosa, A.; Apicella, A.; Aversa, R.; De Rosa, M. Development of Hybrid Materials Based on Hydroxyethylmethacrylate as Supports for Improving Cell Adhesion and Proliferation. *Biomaterials* 2004, 25, 3645-3653.

(52) Nicodemus, G. D.; Bryant, S. J. Cell Encapsulation in Biodegradable Hydrogels for Tissue Engineering Applications. *Tissue Eng Part B Rev.* 2008, 14, 149-165.

(53) Hem, D. L.; Hubbell, J. A. Incorporation of Adhesion Peptides into Nonadhesive Hydrogels Useful for Tissue Resurfacing. *J Biomed Mater Res.* 1998, 39, 266-276.

(54) Almany, L.; Seliktar, D. Biosynthetic Hydrogel Scaffolds Made from Fibrinogen and Polyethylene Glycol for 3D Cell Cultures. *Biomaterials.* 2005, 26, 2467-2477.

(55) Kutty, J. K.; Cho, E.; Lee, J. S.; Vyavahare, N. R.; Webb, K. The Effect of Hyaluronic Acid Incorporation on Fibroblast Spreading and Proliferation within PEG-Diacrylate Based Semi-Interpenetrating Networks. *Biomaterials.* 2007, 28, 4928-4938.

(56) Bencherif, S. A.; Srinivasan, A.; Horkay, F.; Hollinger, J. O.; Matyjaszewski, K.; Washburn, N. R. Influence of the Degree of Methacrylation on Hyaluronic Acid Hydrogels Properties. *Biomaterials* 2008, 29, 1739-1749.

(57) Markstedt, K.; Mantas, A.; Tournier, I.; Martinez Ávila, H.; Hagg, D.; Gatenholm, P. 3D Bioprinting Human Chondrocytes with Nanocellulose-Alginate Bioink for Cartilage Tissue Engineering Applications. *Biomacromolecules* 2015, 16, 1489-1496.

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A hydrogel composition comprising a triblock copolymer having a formula A-B-A, wherein A is a polycaprolactone (PCL) block or a polyvalerolactone (PVL) block and B is a polyethylene glycol (PEG) block, wherein the PEG block B has a molecular weight ranging from 5,000 Da to 100,000 Da.

2. The hydrogel composition of claim 1, wherein the PEG block B has a molecular weight ranging from 10,000 Da to 100,000 Da.

3. The hydrogel composition of claim 1, wherein A is a polycaprolactone (PCL) block.

4. The hydrogel composition of claim 1, wherein the block A has a molecular weight ranging from 200 Da to 10,000 Da.

5. The hydrogel composition of claim 4, wherein the PEG block is a linear PEG polymer.

6. The hydrogel composition of claim 1, wherein the triblock copolymer comprises one or more acrylate, methacrylate, crotonate, vinyl, or norbornene moieties.

7. The hydrogel composition of claim 1, wherein the triblock copolymer is crosslinked by a free radical polymerization.

8. The hydrogel composition of claim 1, wherein the hydrogel is a single-network matrix.

9. The hydrogel composition of claim 1, wherein the composition is biodegradable and biocompatible.

10. The hydrogel composition of claim 1, further comprising one or more viable cells.

11. The hydrogel composition of claim 1, wherein the composition further comprises α-cyclodextrin (α-CD).

* * * * *